(12) United States Patent
Jain et al.

(10) Patent No.: US 12,387,622 B2
(45) Date of Patent: Aug. 12, 2025

(54) SYSTEMS AND METHODS FOR MODELING VEINS AND ASSOCIATED BLOOD VESSEL COMPONENTS

(71) Applicant: The Texas A&M University System, College Station, TX (US)

(72) Inventors: Abhishek Jain, Cypress, TX (US); Navaneeth Krishna Rajeeva Pandian, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 18/739,567

(22) Filed: Jun. 11, 2024

(65) Prior Publication Data

US 2024/0331572 A1 Oct. 3, 2024

Related U.S. Application Data

(63) Continuation of application No. 16/778,947, filed on Jan. 31, 2020, now Pat. No. 12,039,885.

(60) Provisional application No. 62/800,163, filed on Feb. 1, 2019.

(51) Int. Cl.
*G09B 23/32* (2006.01)
*C12N 5/071* (2010.01)
*G09B 23/30* (2006.01)

(52) U.S. Cl.
CPC .......... *G09B 23/306* (2013.01); *C12N 5/069* (2013.01); *G09B 23/303* (2013.01); *G09B 23/32* (2013.01)

(58) Field of Classification Search
None
See application file for complete search history.

(56) References Cited

U.S. PATENT DOCUMENTS

2008/0183280 A1\* 7/2008 Agnew ................. A61F 2/2475
623/1.24

FOREIGN PATENT DOCUMENTS

WO WO-2016004394 A1 \* 1/2016 ........ B01L 3/502738

\* cited by examiner

*Primary Examiner* — James B Hull
(74) *Attorney, Agent, or Firm* — Conley Rose, P.C.

(57) ABSTRACT

A microfluidic chip for modelling flow through a vein includes a body including a microchannel extending between a fluid inlet and a fluid outlet, wherein at least a portion of the microchannel is coated with endothelial cells that form vascular lumen, and a venous valve formed in the body and positioned along the microchannel, wherein the venous valve includes a pair of leaflets defining a pair of cusps of the venous valve, and a flow channel positioned between the leaflets.

20 Claims, 21 Drawing Sheets

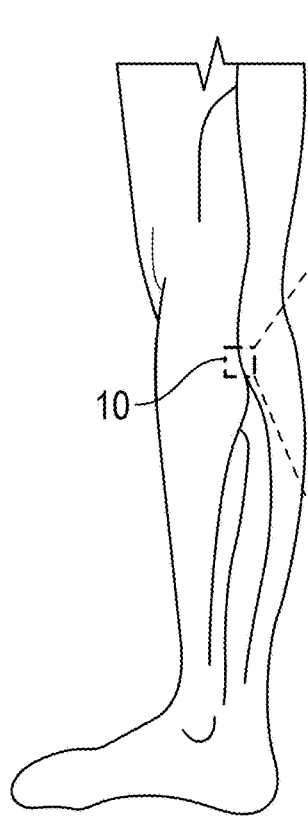 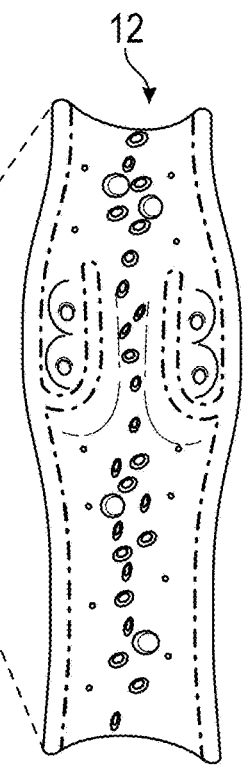 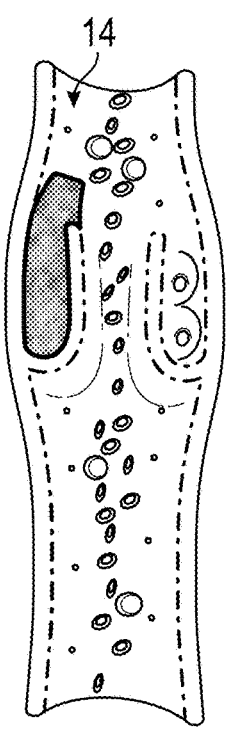 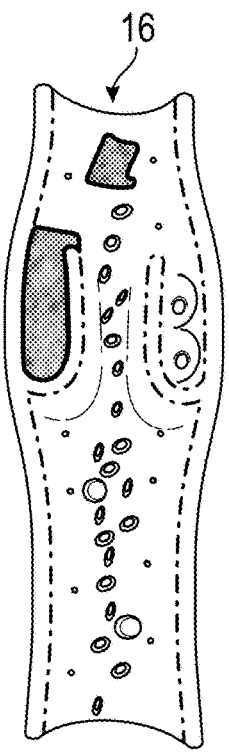
FIG. 1A  FIG. 1B  FIG. 1C  FIG. 1D
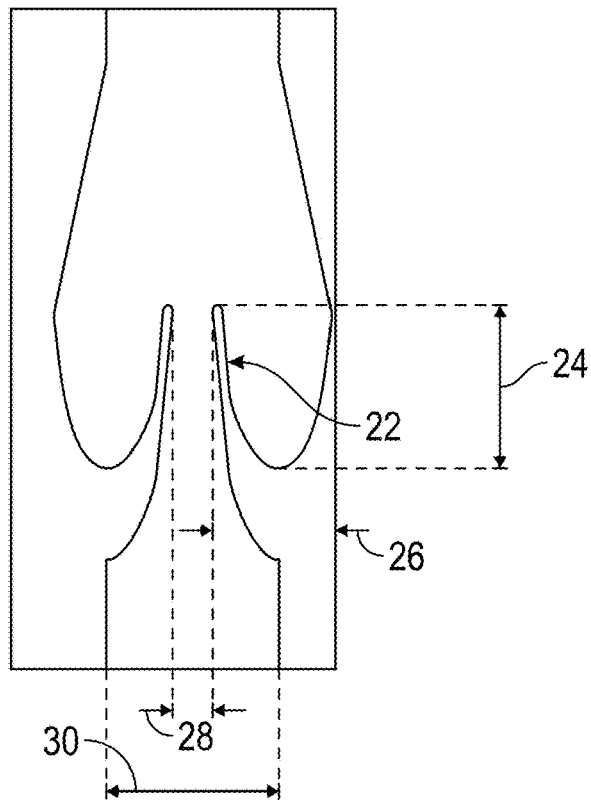
FIG. 2

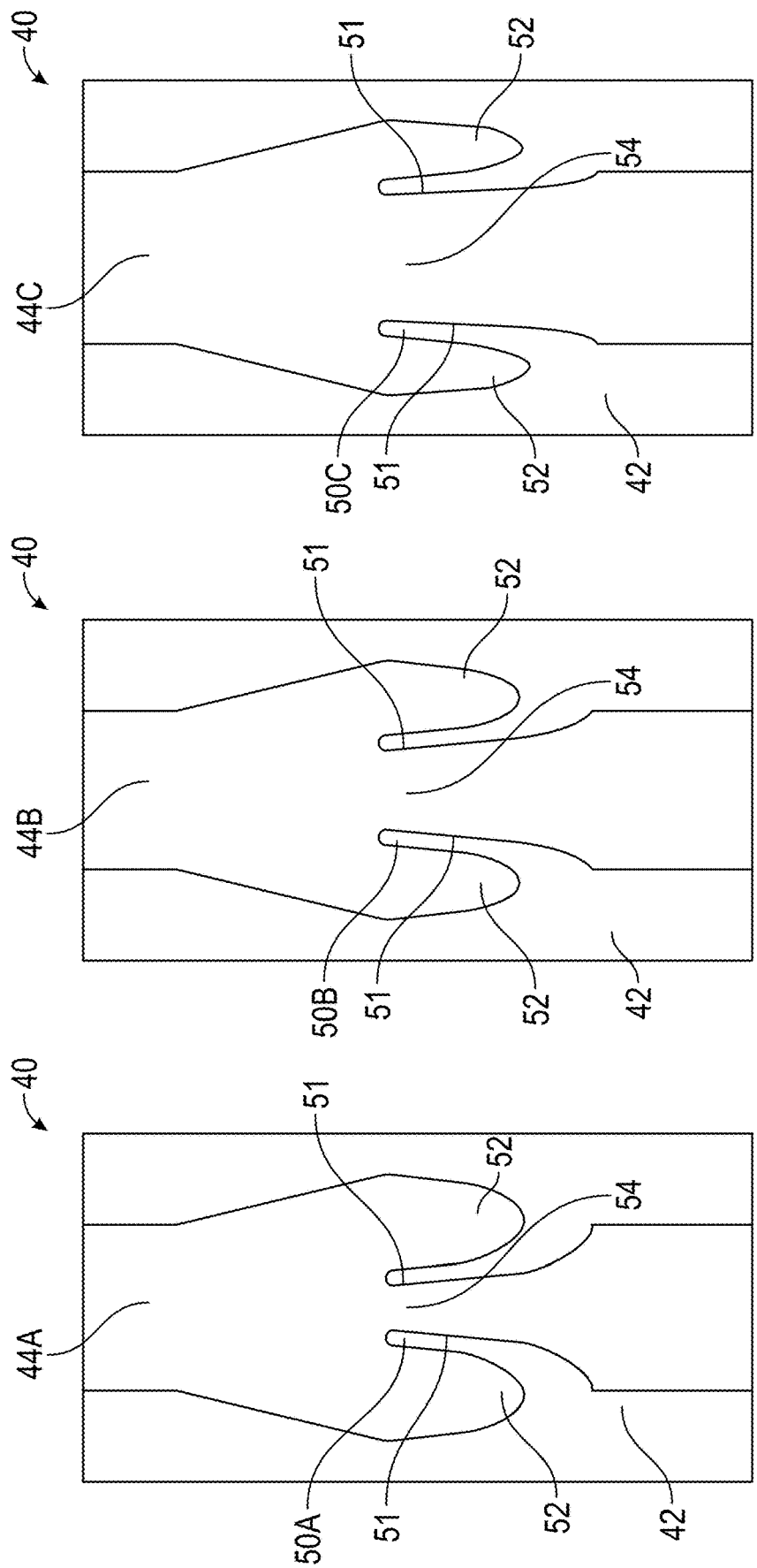

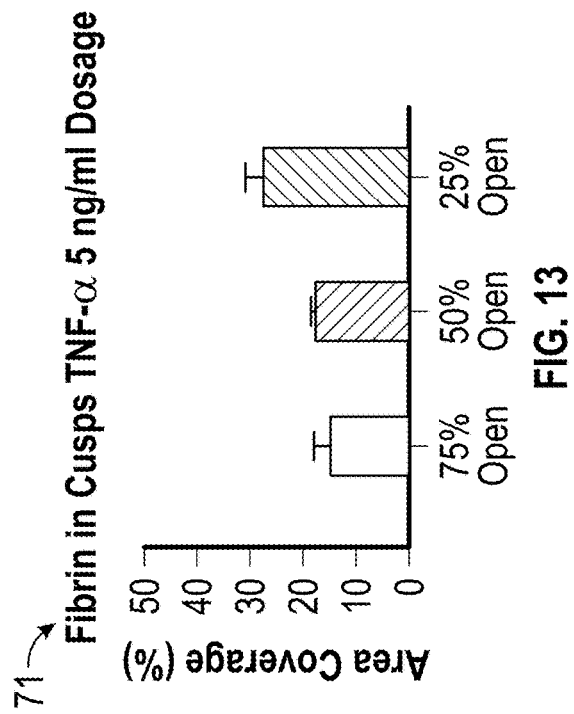
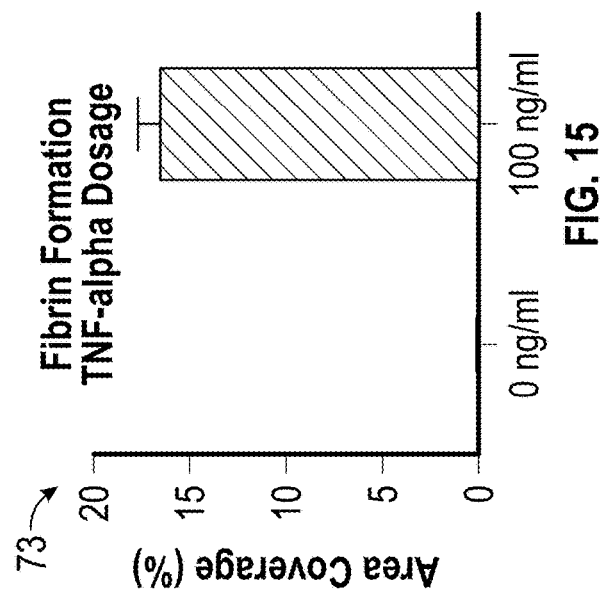
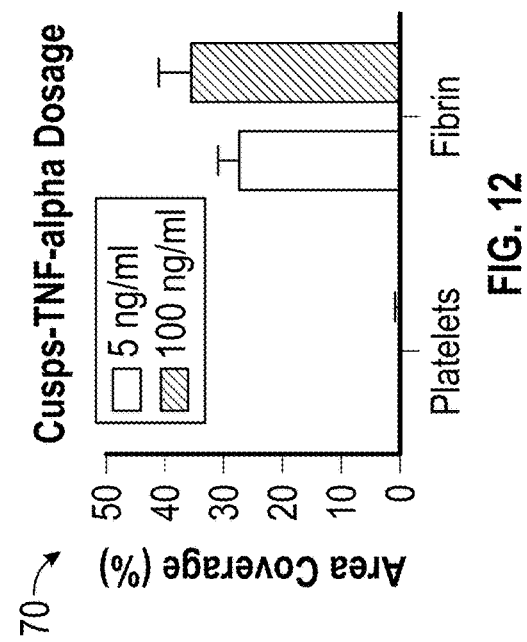
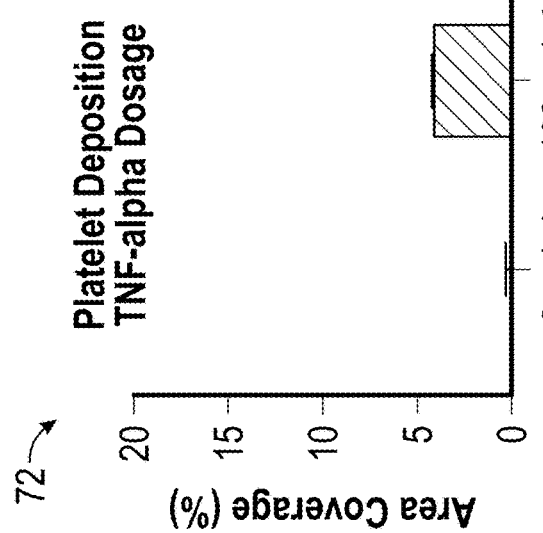

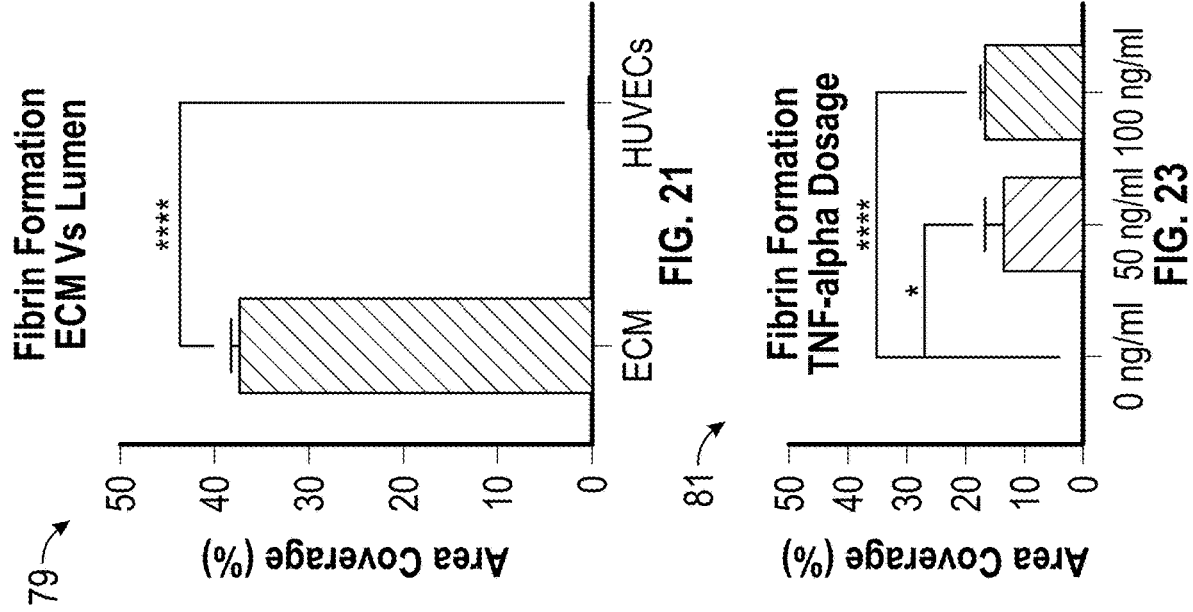
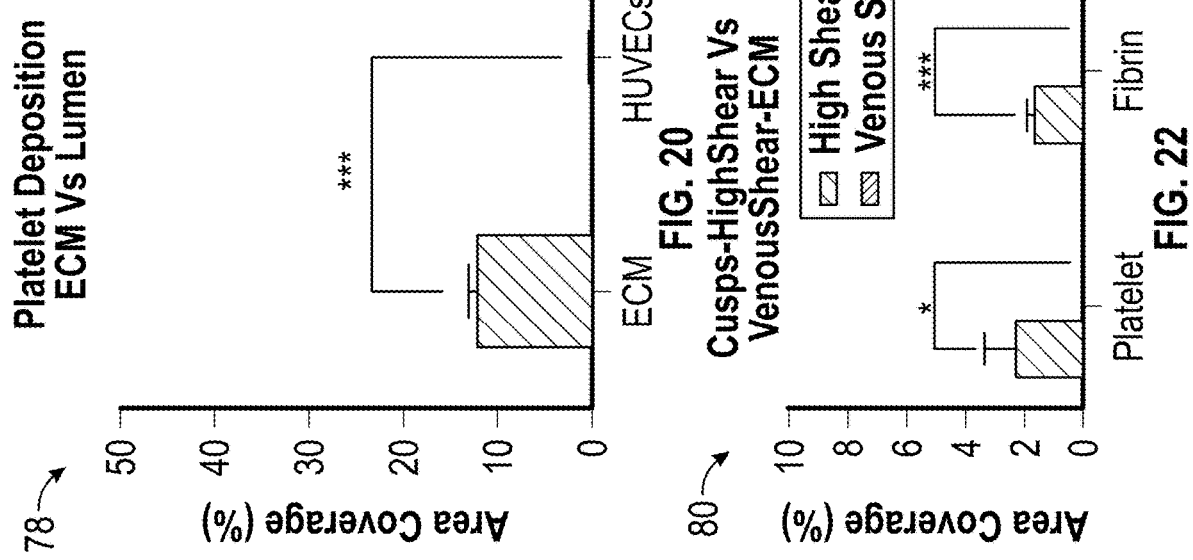

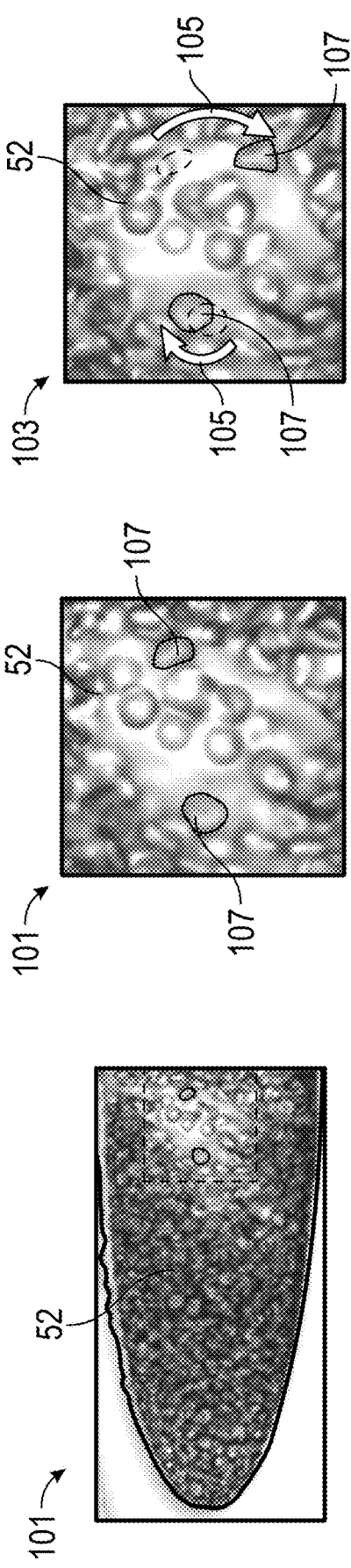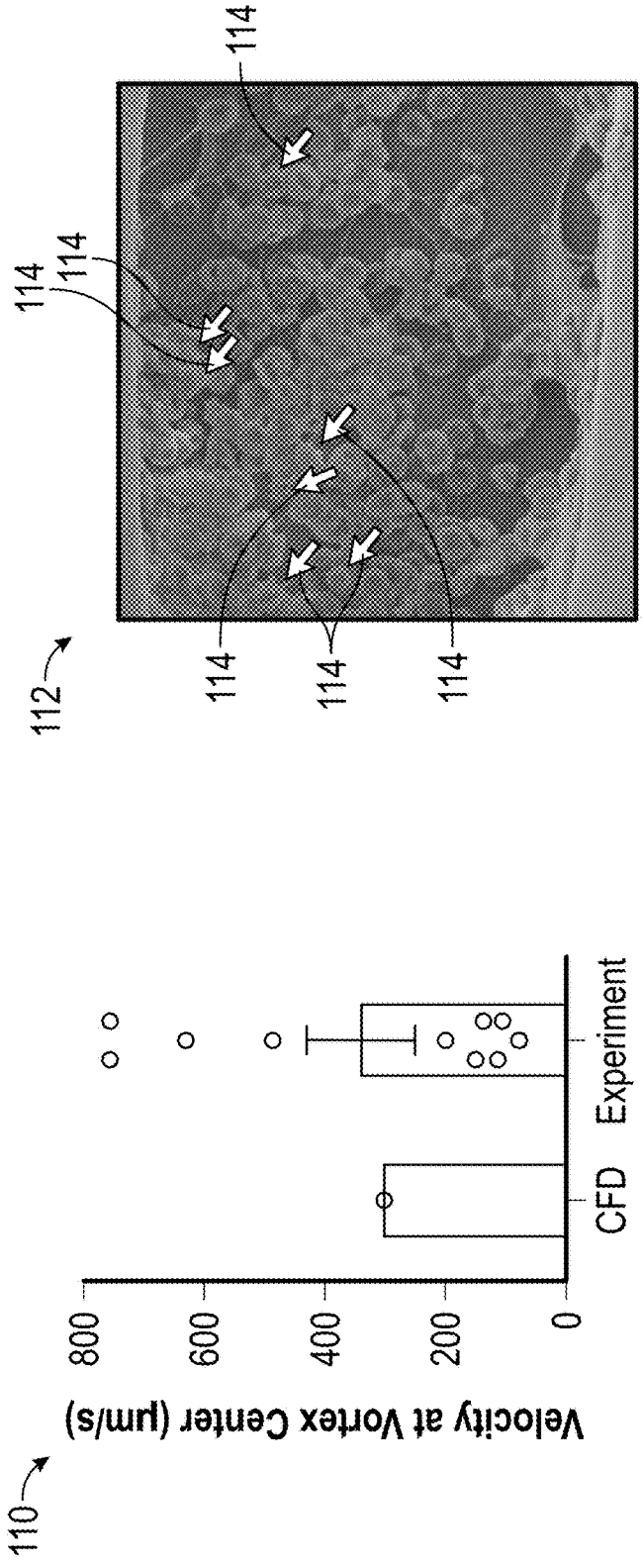
FIG. 31
FIG. 32
FIG. 33
FIG. 34
FIG. 35

SYSTEMS AND METHODS FOR MODELING VEINS AND ASSOCIATED BLOOD VESSEL COMPONENTS

CROSS-REFERENCE TO RELATED APPLICATIONS

This application is a continuation of U.S. non-provisional patent application Ser. No. 16/778,947 filed Jan. 31, 2020, entitled "Systems and Methods for Modeling Veins and Associated Blood Vessel Components" which claims benefit of U.S. provisional patent application No. 62/800,163 filed Feb. 1, 2019, and entitled "Systems and Methods for Modeling Veins and Associated Blood Vessel Components," both of which are hereby incorporated herein by reference in their entirety.

STATEMENT REGARDING FEDERALLY SPONSORED RESEARCH OR DEVELOPMENT

Not applicable.

BACKGROUND

The structural, functional and environmental complexity of the venous blood vessels poses certain technical challenges for in vitro investigation of its physiology and pathology using traditional cell culture models. As a result, most research in this area has relied on expensive and time-consuming ex vivo or in vivo animal studies that can often fail to model biological responses in humans. These drawbacks of existing models can limit the understanding and the development of new therapeutic approaches to diseases of the vein such as deep vein thrombosis.

For example, venous thrombi or blood clots may form at the sites of venous valves, the venous thrombi comprising a unique anatomy and where the behavior of blood flow venous thrombi may be extremely complex. Particularly, deep vein thrombosis (DVT) is a serious debilitating condition, often killing patients within thirty days of its onset. The venous thrombi originate inside venous valves and are generally regulated through vascular activation and shape, unique blood flow and/or abnormal blood chemistry—three factors known as Virchow's triad. However, existing models cannot predict the regulation of blood clots due to the non-involvement of shape of the valves, flow and the composition of cells within the existing models. Additionally, animal models cannot provide a dissectible analysis of the Virchow's triad and may often lead to poor predictions of mechanisms of DVT and drugs.

BRIEF SUMMARY OF THE DISCLOSURE

An embodiment of a microfluidic chip for modelling flow through a vein comprises a body comprising a microchannel extending between a fluid inlet and a fluid outlet, wherein at least a portion of the microchannel is coated with endothelial cells that form vascular lumen, and a venous valve formed in the body and positioned along the microchannel, wherein the venous valve comprises a pair of leaflets defining a pair of cusps of the venous valve, and a flow channel positioned between the leaflets. In some embodiments, the endothelial cells comprise human umbilical vein endothelial cells (HUVECs). In some embodiments, the HUVECs are coated over a layer of an extracellular matrix (ECM). In certain embodiments, the vascular lumen is treated with tumor necrosis-factor alpha (TNF-α) at a dosage of less than 300 nanograms per milliliter (ng/ml). In certain embodiments, at least a portion of the pair of cusps is coated with the endothelial cells that form the vascular lumen. In some embodiments, a width of the flow channel of the venous valve is between 25 micrometers (μm) and 200 μm. In some embodiments, the body is formed from Polydimethylsiloxane (PDMS).

An embodiment of a method of forming a microfluidic chip for modelling flow through a vein comprises (a) forming a microchannel and a venous valve positioned along the microchannel in a master mold, wherein the venous valve comprises a pair of leaflets defining a pair of cusps of the venous valve, and a flow channel positioned between the leaflets, and (b) coating at least a portion of the microchannel with endothelial cells that form vascular lumen. In certain embodiments, the endothelial cells comprise human umbilical vein endothelial cells (HUVECs) coated over a layer of an extracellular matrix (ECM). In certain embodiments, (b) comprises treating the vascular lumen with tumor necrosis-factor alpha (TNF-α) at a dosage of less than 300 nanograms per milliliter (ng/ml).

An embodiment of a microfluidic chip for modelling flow through a vein comprises a body having a central axis and a fluid channel extending between a fluid inlet and a fluid outlet formed in the body, wherein the fluid channel is defined by a pair of channel walls, and wherein at least a portion of the fluid channel is coated with endothelial cells that form vascular lumen, wherein a first venous valve is formed in the body and positioned along the fluid channel, the first venous valve comprising a pair of leaflets defining a pair of cusps of the first venous valve and a flow channel positioned between the leaflets, and wherein a pair of first actuation chambers is positioned adjacent the channel walls of the fluid channel, wherein the pair of first actuation chambers are configured to decrease a width of the flow channel of the first venous valve in response to pressurization of the pair of first actuation chambers, and to increase a width of the flow channel of the first venous valve in response to depressurization of the pair of first actuation chambers. In some embodiments, the body is formed from a three-dimensionally printed material. In some embodiments, the first venous valve comprises a flow channel positioned between the leaflets. In certain embodiments, the pair of first actuation chambers are positioned adjacent a first section of the fluid channel, the body further comprises a pair of second actuation chambers positioned adjacent a second section of the fluid channel located between the first section and the fluid outlet, and wherein the first venous valve is positioned between the first section and the second section, and the leaflets of the first venous valve are configured to direct fluid within the second section of the fluid channel into the cusps of the first venous valve in response to pressurization of the pair of second actuation chambers. In certain embodiments, the body comprises a pair of chamber walls positioned between the first pair of actuation chambers and the second pair of actuation chambers, wherein the pair of chamber walls restrict fluid communication between the first pair of actuation chambers and the second pair of actuation chambers.

An embodiment of a venous valve model comprises a microfluidic chip, wherein a pair of third actuation chambers is positioned adjacent a third section of the fluid channel located between the second section and the fluid outlet, and a second venous valve is formed in the body and positioned between the second section and the third section, and a pumping system comprising a plurality of pumps and configured to simultaneously pressurize the first section and the third section of the fluid channel and depressurize the second section of the fluid channel. In some embodiments, the body comprises a first air channel extending parallel with the fluid channel, and a second air channel extending parallel with the fluid channel, wherein the first air channel, the second air channel, and the fluid channel are each intersected by a plane extending orthogonally from the central axis.

An embodiment of a venous valve model comprises a microfluidic chip, and a pump in fluid communication with at least one of the pair of first actuation chambers, wherein the pump comprises an infusion mode configured to increase a pressure within the at least one of the pair of first actuation chambers to decrease the width of the fluid channel, and a withdraw mode configured to decrease a pressure within the at least one of the pair of first actuation chambers to increase the width of the fluid channel. In some embodiments, the pump comprises a syringe pump. In certain embodiments, the pair of first actuation chambers of the microfluidic chip are positioned adjacent a first section of the fluid channel, the body of the microfluidic chip further comprises a pair of second actuation chambers positioned adjacent a second section of the fluid channel located between the first section and the fluid outlet, and wherein the first venous valve is positioned between the first section and the second section, the leaflets of the first venous valve of the microfluidic chip are configured to direct fluid within the second section of the fluid channel into the cusps of the first venous valve in response to pressurization of the pair of second actuation chambers, the syringe pump comprises a first syringe pump and the venous valve model further comprises a second syringe pump in fluid communication with at least one of the pair of second actuation chambers of the microfluidic chip, the second syringe pump comprises an infusion mode configured to increase a pressure within the at least one of the pair of second actuation chambers to decrease the width of the fluid channel, and a withdraw mode configured to decrease a pressure within the at least one of the pair of second actuation chambers to increase the width of the fluid channel, and the second syringe pump is configured to occupy the withdraw mode when the first syringe pump is in the infusion mode and to occupy the infusion mode when the first syringe pump is in the withdraw mode.

BRIEF DESCRIPTION OF THE DRAWINGS

For a detailed description of exemplary embodiments of the invention, reference will now be made to the accompanying drawings in which:

FIG. 1A is a schematic representation of a human vein;

FIG. 1B is a zoomed-in schematic representation of the human vein of FIG. 1A having normal blood flow;

FIG. 1C is a zoomed-in schematic representation of the human vein of FIG. 1A having DVT;

FIG. 1D is a zoomed-in schematic representation of the human vein of FIG. 1A having an embolism;

FIG. 2 is a schematic representation of a venous valve;

FIGS. 3-5 are schematic representations of an embodiment of a microfluidic chip in accordance with principles disclosed herein;

FIGS. 12-30 are graphs illustrating experimental data pertaining to embodiments of venous valves of the microfluidic chip of FIG. 4 in accordance with principles disclosed herein;

FIGS. 31-33 are Brightfield microscopic images of an embodiment of a venous valve of the microfluidic chip of FIG. 4 in accordance with principles disclosed herein;

FIG. 34 is a graph illustrating experimental data pertaining to the venous valve shown in FIGS. 31-33;

FIG. 35 is a scanning electroscope micrograph of the venous valve shown in FIGS. 31-33;

DETAILED DESCRIPTION OF THE PREFERRED EMBODIMENTS

Figure 6:
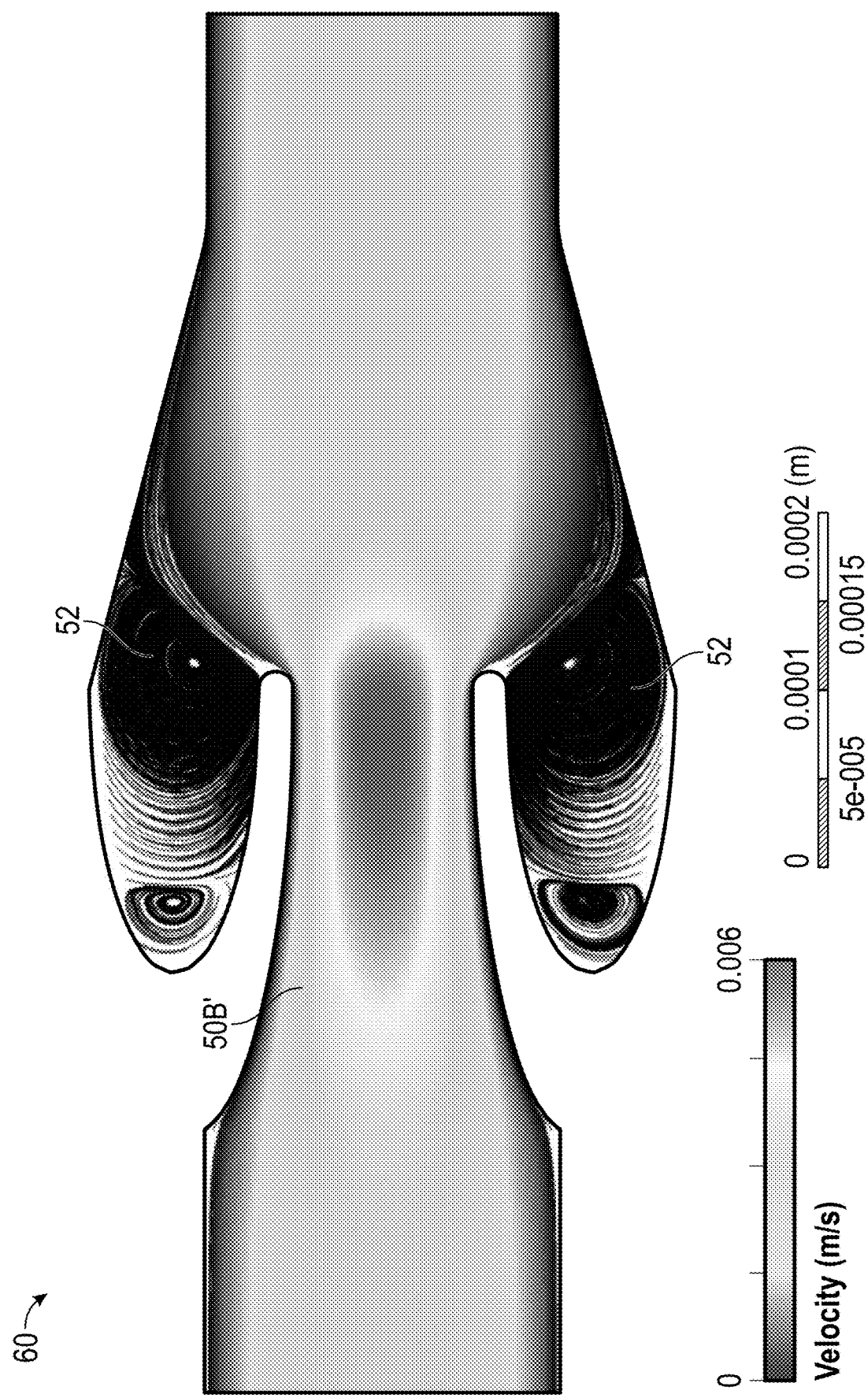
FIG. 6 is a graphical illustration of simulated fluid flow through an embodiment of a venous valve of the microfluidic chip of FIGS. 3-5 in accordance with principles disclosed herein.
Figure 7:
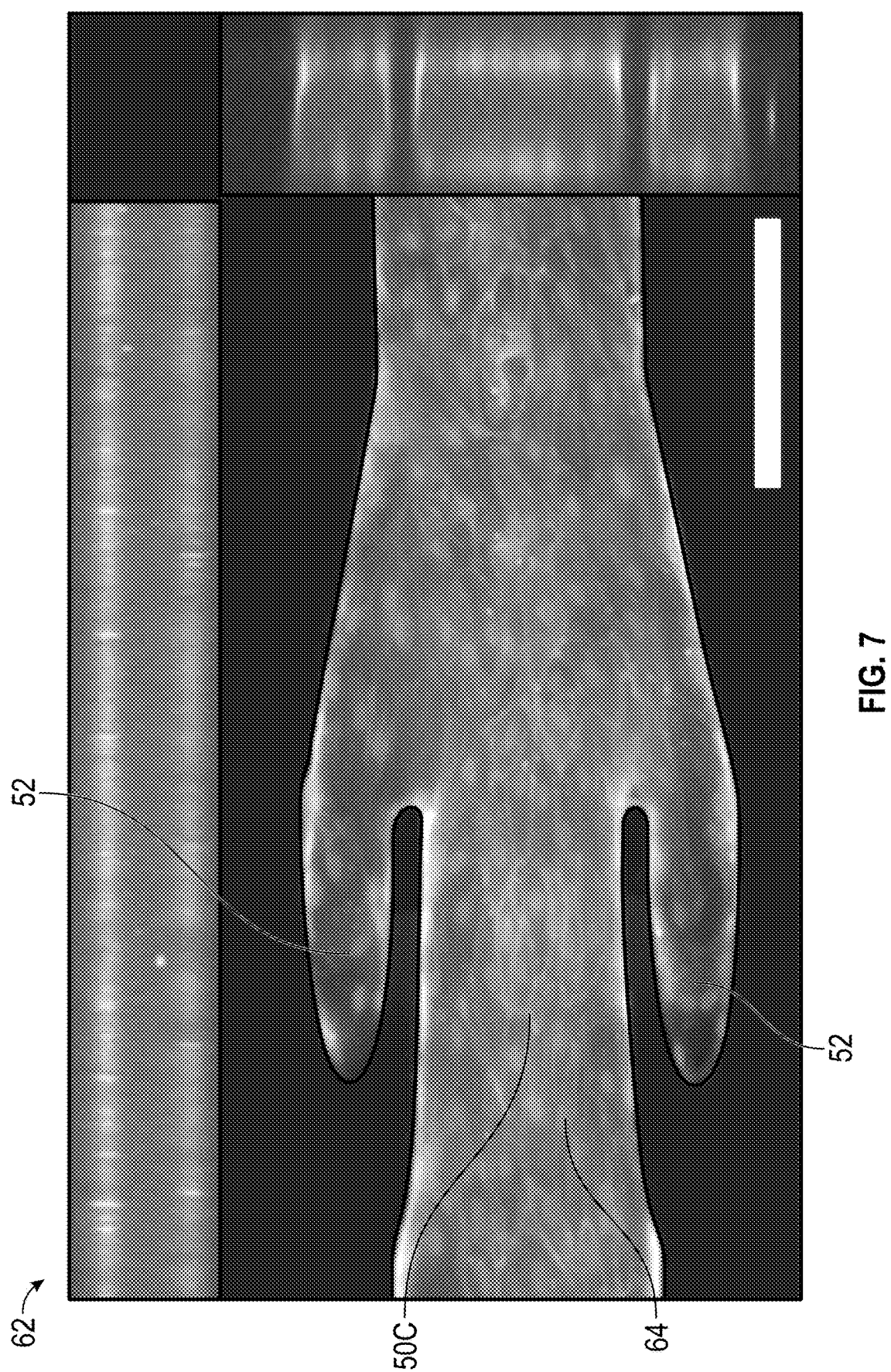
FIG. 7 is an image indicating the fully formed endothelium in the microfluidic chip of FIGS. 3-5.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct engagement between the two devices, or through an indirect connection that is established via other devices, components, nodes, and connections. In addition, as used herein, the terms "axial" and "axially" generally mean along or parallel to a particular axis (e.g., central axis of a body or a port), while the terms "radial" and "radially" generally mean perpendicular to a particular axis. For instance, an axial distance refers to a distance measured along or parallel to the axis, and a radial distance means a distance measured perpendicular to the axis. Any reference to up or down in the description and the claims is made for purposes of clarity, with "up", "upper", "upwardly", "uphole", or "upstream" meaning toward the surface of the borehole and with "down", "lower", "downwardly", "downhole", or "downstream" meaning toward the terminal end of the borehole, regardless of the borehole orientation. As used herein, the terms "approximately," "about," "substantially," and the like mean within 10% (i.e., plus or minus 10%) of the recited value. Thus, for example, a recited angle of "about 80 degrees" refers to an angle ranging from 72 degrees to 88 degrees.

Referring to FIGS. 1A-2, as described above, human veins (e.g., human vein 10 shown in FIG. 1A) may, from a condition of normal blood flow 12 (shown schematically in FIG. 1B), develop DVT 14 (shown schematically in FIG. 1C) which may result in potentially fatal venous thromboembolism 16 (shown schematically in FIG. 1D). Ex vivo and in vivo animal studies are generally expensive, time-consuming, and often fail to model biological responses in humans. The present disclosure is directed towards leveraging microengineering technology known as "organ-on-a-chip" for controlling cellular microenvironments with high spatiotemporal precision, and to present living cultured cells with mechanical and biochemical signals in a more physiologically relevant context. By deploying this strategy, in vitro models of diseases of the human veins may be developed that include a design and biological complexity similar to that of human veins. The organ-on-a-chip methodologies disclosed herein offer a more physiologically-relevant human disease modeling platform for DVT 10. Particularly, a micro-physiological DVT-on-a-chip is disclosed herein that is a mouse-scale model of a vein containing a venous valve 20 (represented schematically in FIG. 2) comprising a valve leaflet 22 and having a sinus depth 24, a sinus width 26, a gap width 28, and a channel width 30. The DVT-on-a-chip disclosed herein allows for the independent or cooperative perturbing of Virchow's triad—endothelial valve architecture and state of activation (including hypoxia), whole blood flow, and blood cells and coagulation factors/proteins to thereby permit dissectible analysis of DVT.

Referring to FIGS. 1A-5, an embodiment of a vein-on-a-chip, venous valve model, or microfluidic chip 40 is shown schematically in FIGS. 3-5. Microfluidic chip 40 comprises a chip or body 42 through which three separate fluid microchannels 44A, 44B, and 44C linearly extend (microchannels 44A-44C are shown separately in FIGS. 3-5, respectively). Each microchannel 44A, 44B, 44C includes a fluid inlet, a fluid outlet, and a plurality of venous valve 50A, 50B, and 50C, respectively.

Particularly, in the embodiment of FIGS. 3-5, first fluid channel 44A includes three first venous valves 50A (only one of which is shown in FIG. 3), second fluid channel 44B includes three second venous valves 50B (only one of which is shown in FIG. 4), and third fluid channel 44C includes three third venous valves 50C (only one of which is shown in FIG. 5). Each venous valve 50A-50B comprises a pair of valve leaflets 51 defining cusps 52, and a central flow channel 54 extending between the pair of leaflets 51.

In this embodiment, each first venous valve 50A is 25% open (e.g., having a gap width across flow channel 54 of about 50 micrometers ($\mu$m)), each second venous valve 50B is 50% open (e.g., having a gap width of about 200 $\mu$m), and each third venous valve 50C is 75% open (e.g., having a gap width of about 150 $\mu$m). In this embodiment, body 42 of microfluidic chip 40 is about 75 millimeters (mm) long and 25 mm wide. Additionally, in this embodiment, each microchannel 44A-44C is about two centimeters (cm) long, about 200 $\mu$m wide, and about 75 $\mu$m in height, which may be similar in size and geometry as a mouse vein. Further, in this embodiment, each venous valve 50A-50C spaced about 0.5 cm apart along microchannels 44A-44C, respectively. In some embodiments, body 12 is formed from polydimethylsiloxane (PDMS), a silicon-based organic polymer, via soft lithography. One or more pumps may be coupled to microchannels 44A-44C for flowing or directing fluid through each microchannel 44A-44C. Additionally, a microscope may be positioned over each venous valve 50A-50C of each microchannel 44A-44C, respectively, for monitoring fluid flow through venous valves 50A-50C.

In this embodiment, to form microfluidic chip 40, microelectronic and semiconductor fabrication techniques were used to develop an SU-8 photoresist-based master mold. Particularly, computational fluid dynamics simulations were carried out to arrive at the open venous valve designs (e.g., venous valves 50A-50C) which contained recirculations as observed in venous valve cusps in vivo. The embodiments of the finalized venous valve designs shown in FIGS. 3-5 were developed using solid modeling computer-aided design (CAD) software (e.g., the SolidWorks™ software package published by Dassault Systemes) and a photomask of the finalized valve designs was used to fabricate the master mold using epoxy-based negative photoresist—SU-8 on a silicon wafer in this embodiment. In this embodiment for forming microchannels 44A-44C, once the master molds were fabricated, the wafers were treated with Silane, and Polydimethylsiloxane (PDMS) having an epoxy to crosslinker ratio of about 10:1 was poured into the master mold. In this embodiment, once the PDMS was set, the PDMS was striped and bonded to a PDMS coated glass slide to form microchannels 44A-44C, each microchannel 44A-44C having PDMS coated on each side thereof. Additionally, PDMS, being hydrophobic, was treated with plasma and then silanized with (3-aminopropyl) triethoxylsilane (APTES) to make the PDMS hydrophilic. In this embodiment, microchannels 44A-44C were then filled with type-I rat tail collagen of about 200 micrograms per milliliter (ug/ml) and fibronectin of about 50 ug/ml to form an extracellular matrix (ECM) configured to support endothelial cell growth on the walls of each microchannel 44A-44C.

In this embodiment for forming microchannels 44A-44C, human umbilical vein endothelial cells (HUVECs) were cultured over a layer of the ECM coated on microchannels 44A-44C; however, in other embodiments, human or animal cell lines other than HUVECs may also be used in the formation of microchannels 44A-44C. In this embodiment, HUVECs, a human primary cell line derived from the human umbilical vein, were acquired and seeded on T75 flasks coated with type I rat tail collagen of about 5 micrograms (μg) per 5 $cm^2$, the HUVECs being seeded at about 50,000 cells per flask. In this embodiment, the endothelial growth media (EGM) (EGM-2 MV, promocell in this embodiment) disposed in the flasks were replaced every two days, and once the flasks were 80% confluent, the HUVECs were detached from the flasks and seeded on microchannels 44A-44C with about 20-30 microliters (μl) of cell suspension having cell density of about 1e7 cells per milliliter (ml). The cell suspension was passed through a cell strainer to remove debris and cell aggregates that were larger than about 40 μm in diameter. In this embodiment, microchannels 44A-44C were then first filled with cell suspension and kept upside down for about 20 minutes to seed the top face of microchannels 44A-44C, and then microchannels 44A-44C were again filled with cell suspension and kept upright for 20 minutes to seed the bottom faces of microchannels 44A-44C.

To induce activation, the vascular lumen coated to microchannels 44A-44C was treated with the tumor necrosis factor (TNF) TNF-α at about 0-200 nanograms per milliliter (ng/ml) in this embodiment. Particularly, the seeded microchannels 44A-44C were perfused with media at about 1 ul/min for about 24 hours. Confluent lumen was formed on the walls of microchannels 44A-44C at the end of 24 hours. Additionally, in this embodiment, different doses TNF-α, a cytokine, was introduced into the confluent lumen of the channels for about 18 hours to observe the dose dependent inflammation of the endothelial cells in the straight sections of microchannels 44A-44C and venous valve cusps of venous valves 50A-50C.

Further, in this embodiment of the formation of microchannels 44A-44C, computation fluid dynamics (CFD) simulations of non-Newtonian blood flow were carried out via software (e.g., ANSYS@ software published by Ansys Inc.) to predict disturbed venous blood flow. Particularly, referring to FIGS. 1A-206, CFD simulations were performed for the venous valves 50A-50C of microchannels 44A-44C to analyze the characteristics of non-Newtonian fluid flow therethrough, as shown particularly in FIG. 206. For example, a CFD simulation 60 was performed for second venous valve 50B. The CFD simulation 60 confirmed the formation of secondary vortices and stasis of blood in the valve cusps 52 of the simulated venous valve 50B' (shown in FIG. 6), predicting the tendency of the geometries of simulated venous valve 50B' to form thrombus within valve cusps 52.

In this embodiment of the formation of microchannels 44A-44C, to evaluate role of hypoxia, microfluidic chip 40 was incubated at 3.9% oxygen. Re-calcified citrated blood was perfused through microchannels 44A-44C at a physiological or pathological shear stress (about 0.5-20 dynes per centimeters squared (dynes/$cm^2$) in this embodiment). Additionally, blood coagulation in microchannels 44A-44C was altered by the addition of thrombin or heparin. Fluorescently labelled platelets and fibrin were visualized and quantitated via microscopes positioned adjacent microchannels 44A-44C. Additionally, in this embodiment, typical vascular identity and adhesion markers were measured through immunohistochemistry.

Figure 8:
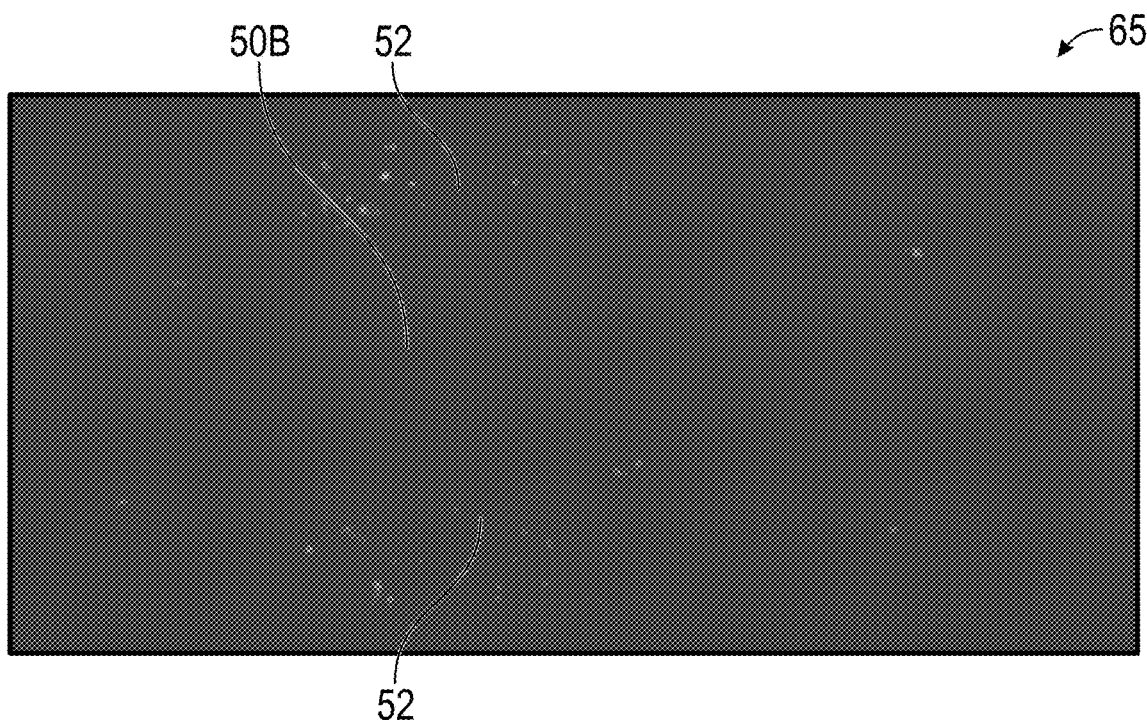
FIG. 8 is an image indicating platelet deposition in an embodiment of a venous valve of the microfluidic chip of FIG. 4 in accordance with principles disclosed herein.
Figure 9:
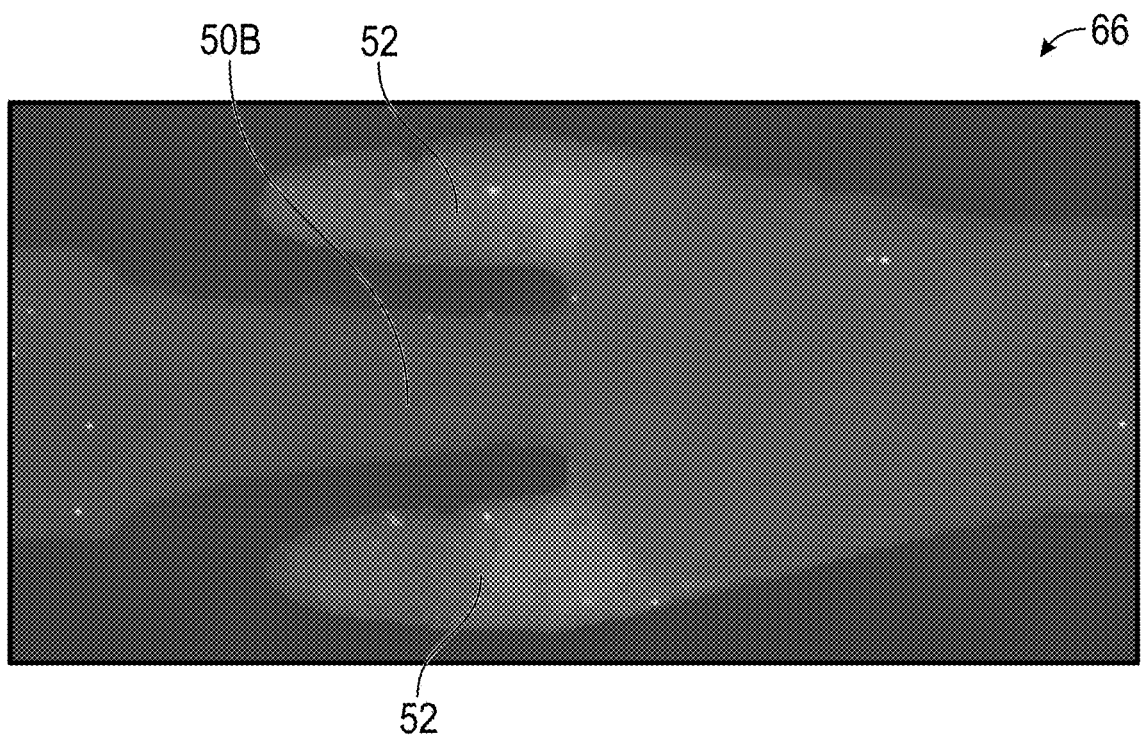
FIG. 9 is an image indicating fibrin/fibrinogen deposition in an embodiment of a venous valve of the microfluidic chip of FIG. 4 in accordance with principles disclosed herein.
Figure 10:
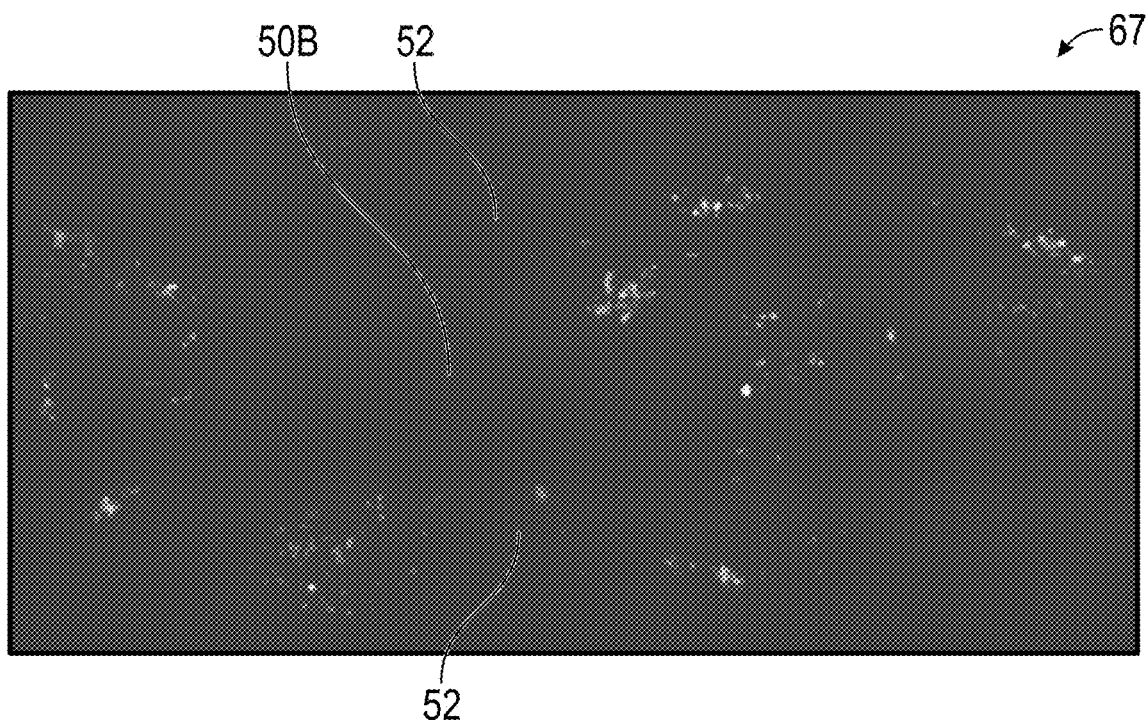
FIG. 10 is another image indicating platelet deposition in the venous valve of FIG. 8.
Figure 11:
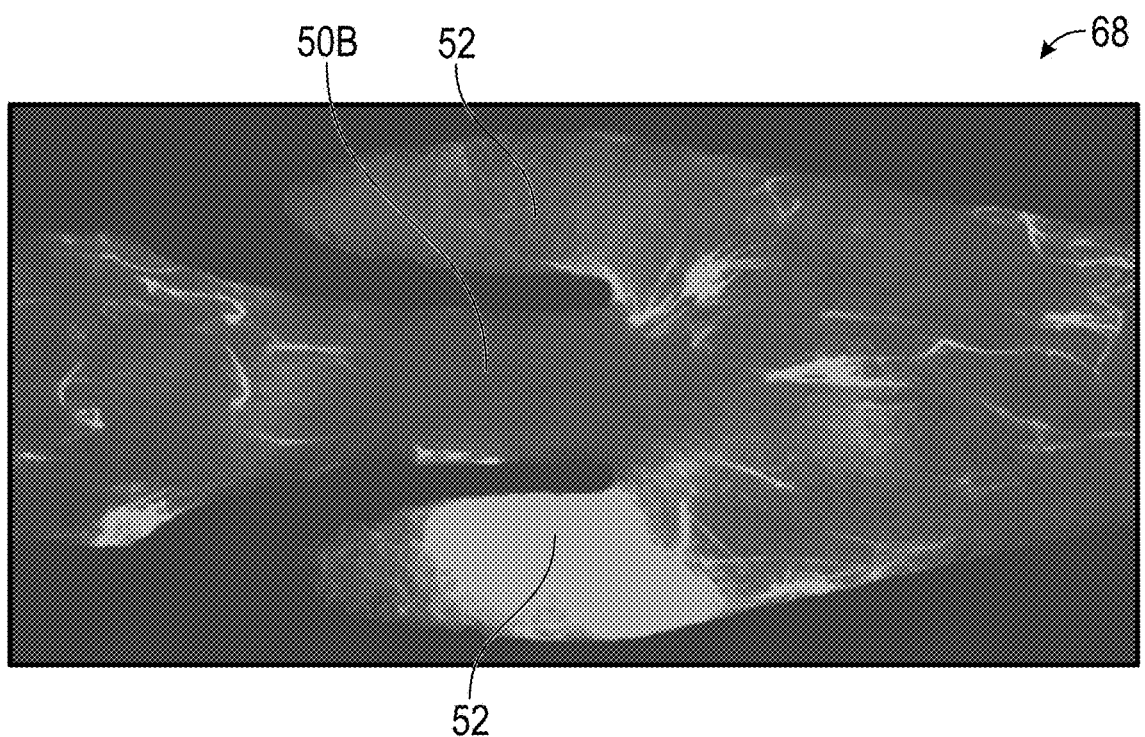
FIG. 11 is another image indicating fibrin/fibrinogen deposition in the venous valve of FIG. 9.

Referring to FIGS. 3-5 and 7-11, exemplary imagery pertaining to experimental whole blood (tagged for platelets and fibrin/fibrinogen) perfusion through embodiments of venous valves 50A-50C is shown in FIGS. 7-11. As shown particularly in image 62 of third venous valve 50C presented in FIG. 7, confluent vascular lumens 64 were cultured within venous valves 50A-50C with expected junction integrity, actin and visible nuclei. In this example, when blood was perfused through the untreated healthy HUVECs shown in venous valves 50A-50C at venous shear of about 0.5 dynes/$cm^2$, no thrombi were detected. For example, image 65 of FIG. 8 illustrates platelets within venous valve 50B while image 66 of FIG. 9 illustrates fibrinogen/fibrin within venous valve 50B. However, upon stimulation of HUVECs with TNF-α (shown in FIGS. 10, 11), thrombi were detected due to the expression of endothelial adhesion proteins. For example, image 67 of FIG. 10 illustrates platelets within venous valve 50B while image 68 FIG. 11 illustrates fibrogen/fibrin within venous valve 50B.

Figure 17:
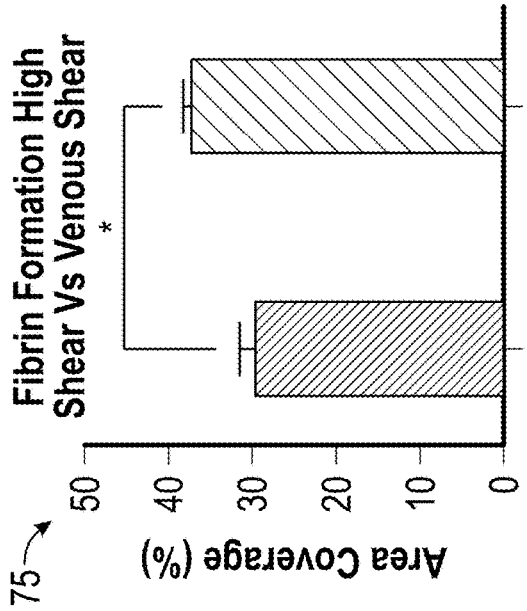
Figure 19:
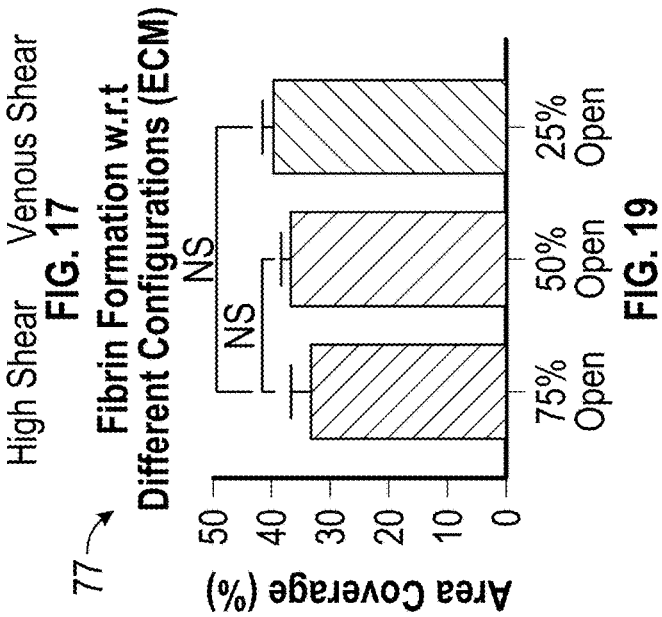
Figure 16:
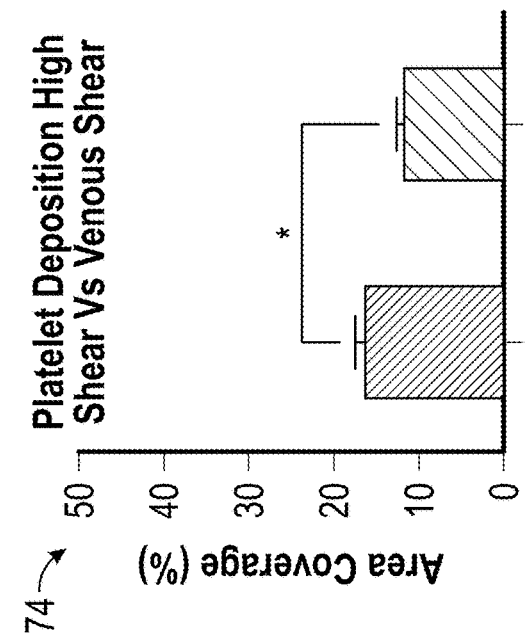
Figure 18:
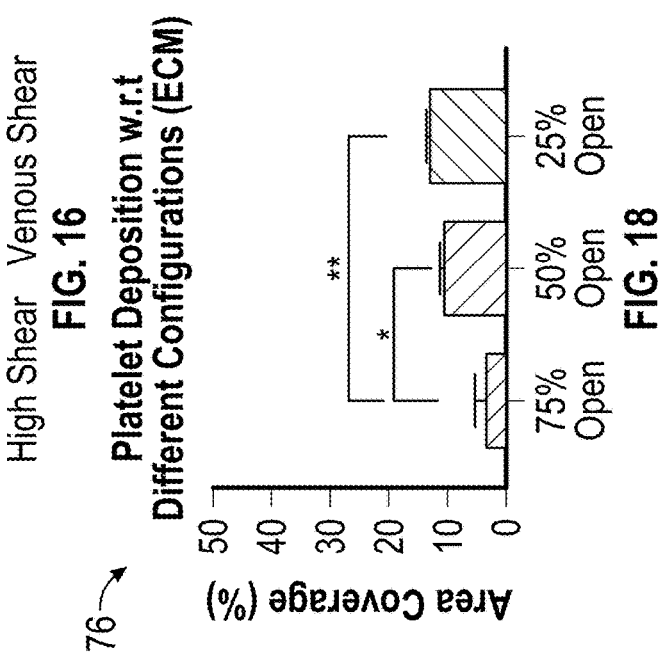

Referring to FIGS. 3-5, 12-30, experimental data pertaining to exemplary perfusion of blood through venous valves 50A-50C is shown in FIGS. 12-30. Particularly, graphs 70, 71 shown in FIGS. 12, 13, respectively, illustrate TNF-α dosage in venous valve 50B and fibrin in cusps 52 of venous valves 50A-50C, while graphs 72, 73 of FIGS. 14, 15, respectively, illustrate platelet distribution and fibrin formation in venous valve 50B. Additionally, graphs 74, 75 shown in FIGS. 16, 17, respectively, illustrate platelet deposition at high shear (about 15 dyne/cm in the exemplary experimental data provided in FIGS. 12-30) and venous shear (about 1 dyne/cm in the exemplary experimental data provided in FIGS. 12-30) and fibrin formation at high shear versus venous shear in venous valve 50B, while graphs 76, 77 shown in FIGS. 18, 19, respectively, illustrate platelet deposition and fibrin formation for each venous valve 50A, 50B, and 50C. Further, graphs 78, 79 shown in FIGS. 20, 21, respectively, illustrate platelet (ECM) distribution and fibrin formation versus lumen (HUVEC) deposition in venous valve 50B.

Figure 24:
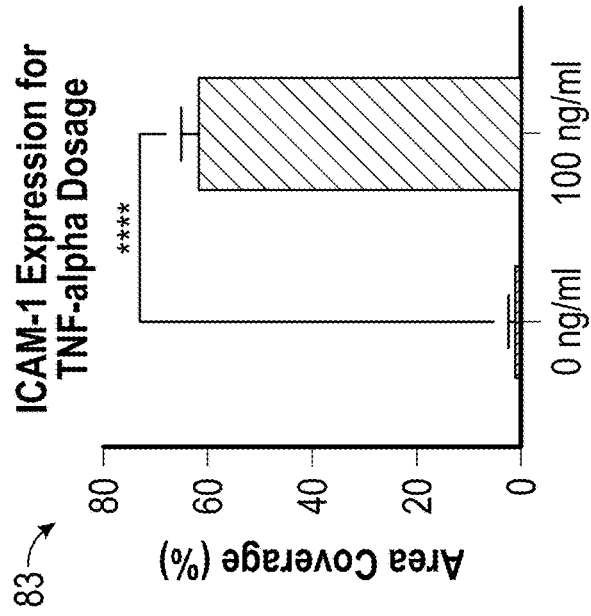
Figure 25:
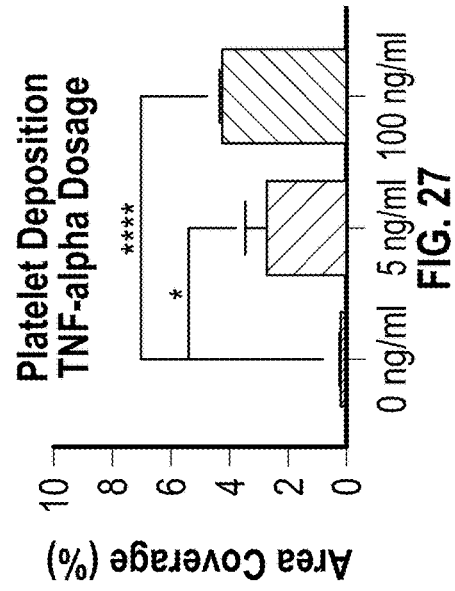
Figure 26:
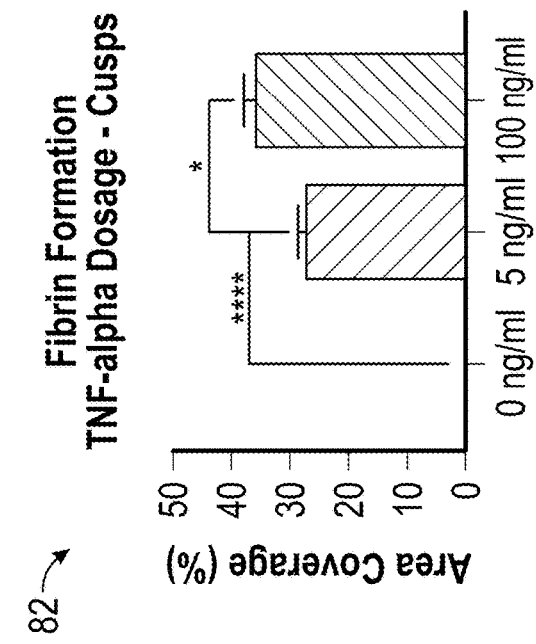
Figure 27:
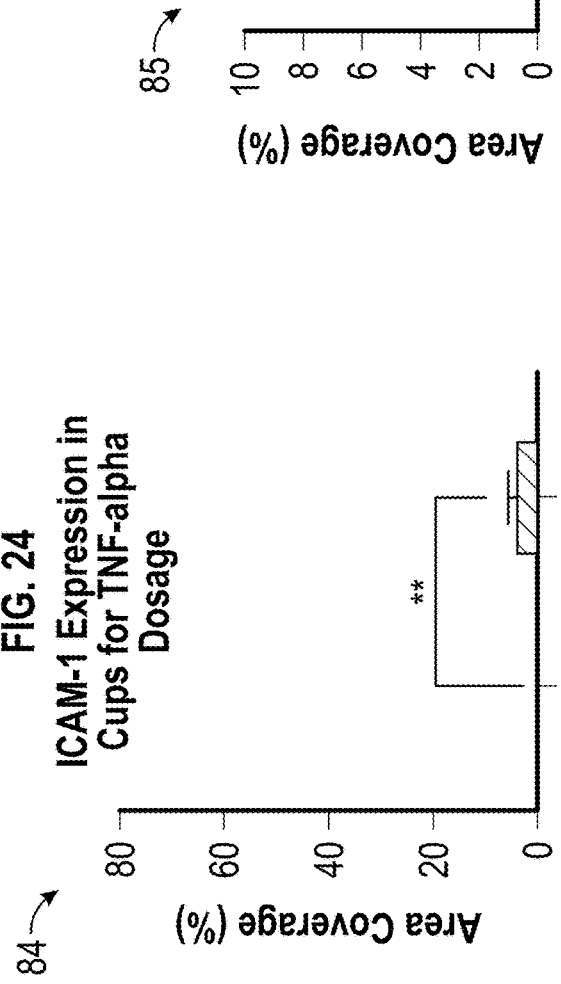
Figure 28:
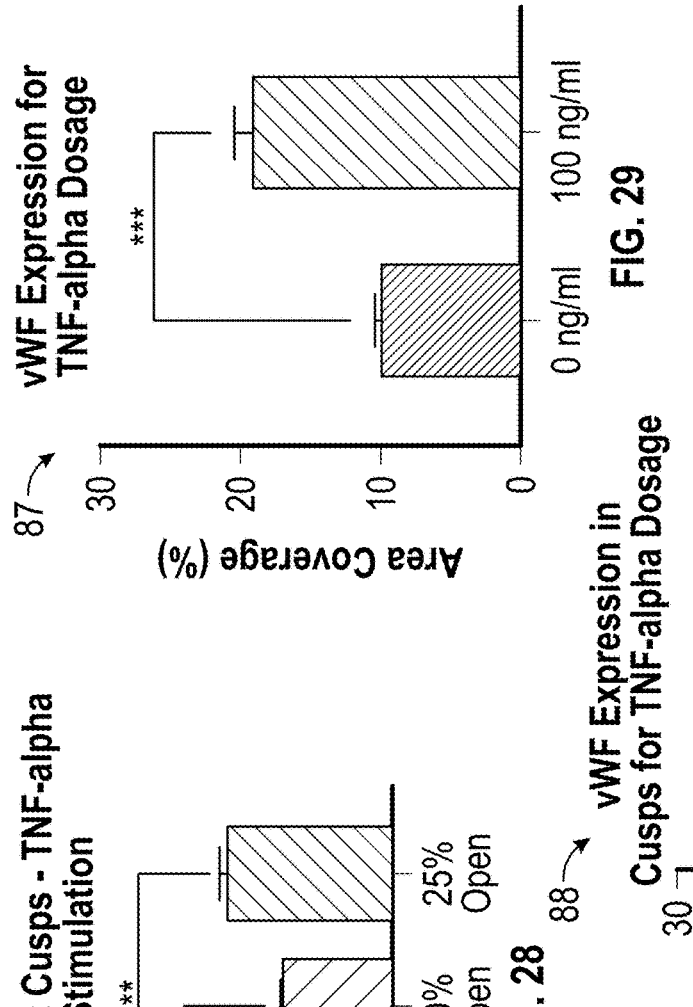
Figure 29:
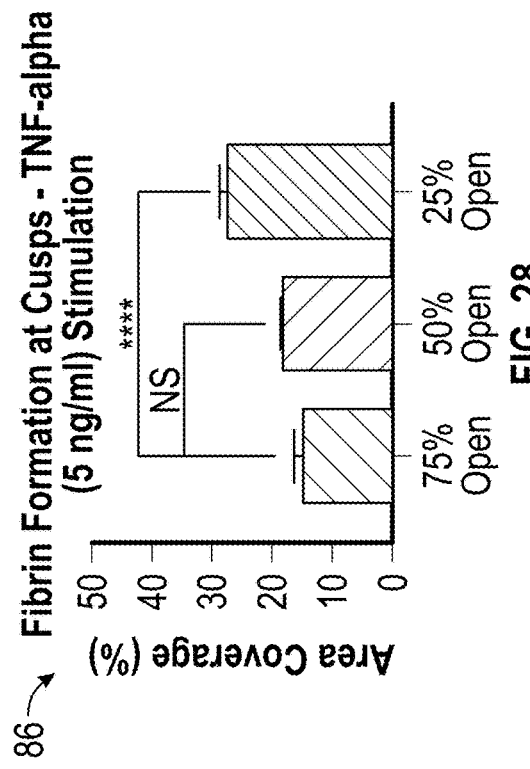
Figure 30:
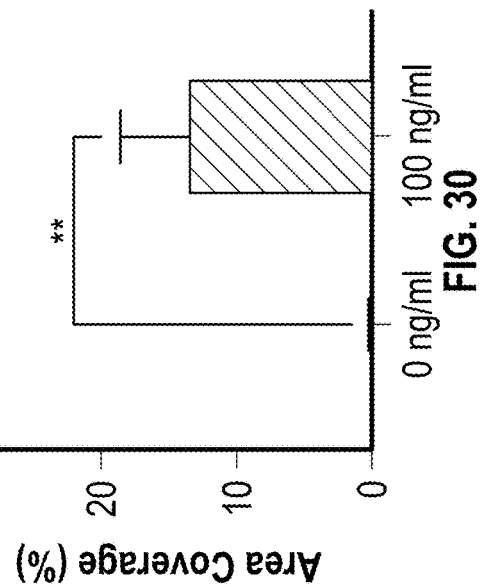

Graph 80 shown in FIG. 22 illustrates both platelet and fibrin coverage within cusps 52 of venous valve 50B for high shear versus venous shear, while graph 81 shown in FIG. 23 illustrates fibrin formation for TNF-α dosages of 0 ng/ml, 5 ng/ml, and 200 ng/ml in venous valve 50B. Graph 82 shown in FIG. 24 illustrates fibrin formation within cusps 52 of venous valve 50B for TNF-α dosages of 0 ng/ml, 5 ng/ml, and 200 ng/ml. Graph 83 shown in FIG. 25 illustrates intercellular adhesion module (ICAM)-I expression for TNF-α dosages of 0 ng/ml, 200 ng/ml in venous valve 50B while graph 84 shown in FIG. 26 illustrates ICAM-1 expression in the cusps 52 of venous valves 50B for TNF-α dosages of 0 ng/ml, 200 ng/ml. Additionally, graph 85 shown in FIG. 27 illustrates platelet deposition within venous valve 50B for TNF-α dosages of 0 ng/ml, 5 ng/ml, and 200 ng/ml, while graph 86 shown in FIG. 28 illustrates fibrin formation within the cusps 52 (at a TNF-α dosage of 5 ng/ml) of each venous valve 50A-50C. Further, graph 87 shown in FIG. 29 illustrates expression of Von Willebrand factor (vWF) within venous valve 50B for TNF-α dosages of 0 ng/ml and 200 ng/ml, while graph 88 shown in FIG. 30 illustrates vWF expression within the cusps 52 of venous valve 50B for TNF-α dosages of 0 ng/ml and 200 ng/ml.

In this example, increased fibrin deposition occurred at the cusps 52 of venous valves 50A-50C and very limited platelet deposition also occurred, which is typical for venous thrombi in vivo. Also in this example, the flow rate of blood flow was varied through microchannels 44A-44C and it was found that thrombi formed in the cusps 52 are flow dependent. At venous shear stress, fibrin-rich thrombi at the cusps were observed in this example whereas platelet adhesion was observed only at high shear. Further, in this example, addition of heparin in blood decreased the thrombi formation within venous valves 50A-50C which was dose dependent.

In view of the above, including the experimental data illustrated in FIGS. 12-30, microfluidic chip 40 provides for the modelling and dissection of critical biophysical and biological processes of DVT unobserved in straight perfusion devices or conventional mouse models. Additionally, microfluidic chip 40 may be used to help unravel specific shear and endothelium driven signaling pathways, and drug-tissue interactions.

Referring to FIGS. 31-35, Brightfield microscopic images 101, 102 of a cusp 52 of an embodiment of venous valve 50B are shown in FIGS. 31-33. Particularly, image 101 shown in FIGS. 31, 32 (FIG. 32 being a zoomed-in view of image 101 shown in FIG. 31, where image 101 in FIG. 31 has a scale of approximately 200 μm in this example) illustrate cusp 52 at a first moment in time while image 103 shown in FIG. 33 (FIG. 33 having the same scale as FIG. 32, approximately 50 μm in this example) illustrate cusp 52 at a second moment in time approximately 0.18 seconds after the first moment. As shown particularly in FIGS. 31-33, the fluid flow pattern, recirculations and secondary vortices were recreated using an embodiment of microfluidic chip 40 similar to that observed in vivo. Particularly, images 101, 103 illustrate the formation of vortices (indicated by arrows 105 in FIG. 33) of red blood cells 107 within cusp 52. In the example shown in FIGS. 31-35, red blood cells 107 follow a circular path in the primary vortex 105. FIG. 34 illustrates a graph 110 comparing velocity within primary vortex 105 as estimated from the experiment shown in FIGS. 31-33 and that projected from CFD analysis.

As shown particularly in FIG. 35, the constituents of thrombi formed in cusp 52 may be analyzed from scanning electron microscope (SEM) images, such as the scanning electroscope micrograph or image 112 shown in FIG. 35. In the example shown in FIG. 35, the formed thrombi were first fixed using paraformaldehyde and then the embodiment of microfluidic chip 40 used in this example was cut open along microfluidic channels 44A-44C. Once cut, microfluidic channels 44A-44C were sputter coated with a layer of gold nanoparticles and imaged in a SEM. Image 112 of thrombi (indicated by arrows 114 in FIG. 35) formed in cusp 52 reinforces that the thrombi 114 are rich in fibrin/red blood cells and devoid of platelets.

Figure 36:
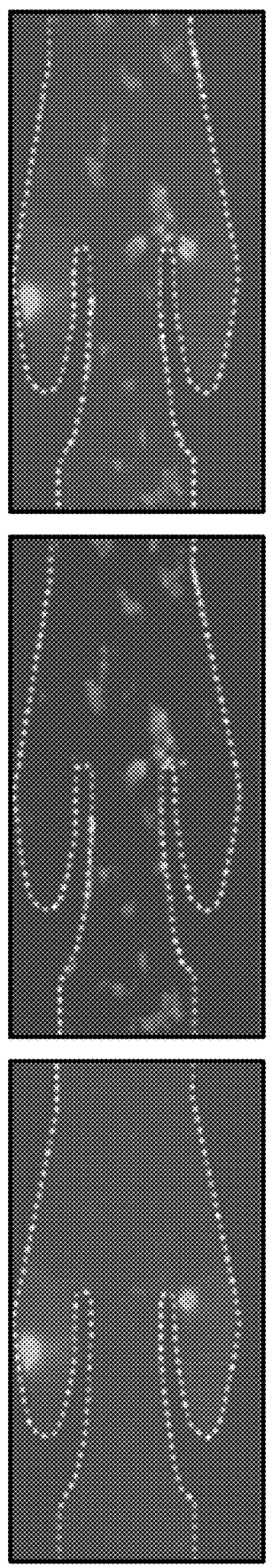
FIGS. 36, 37 are images of an embodiment of a venous valve of the microfluidic chip of FIG. 4 in accordance with principles disclosed herein.
Figure 37:
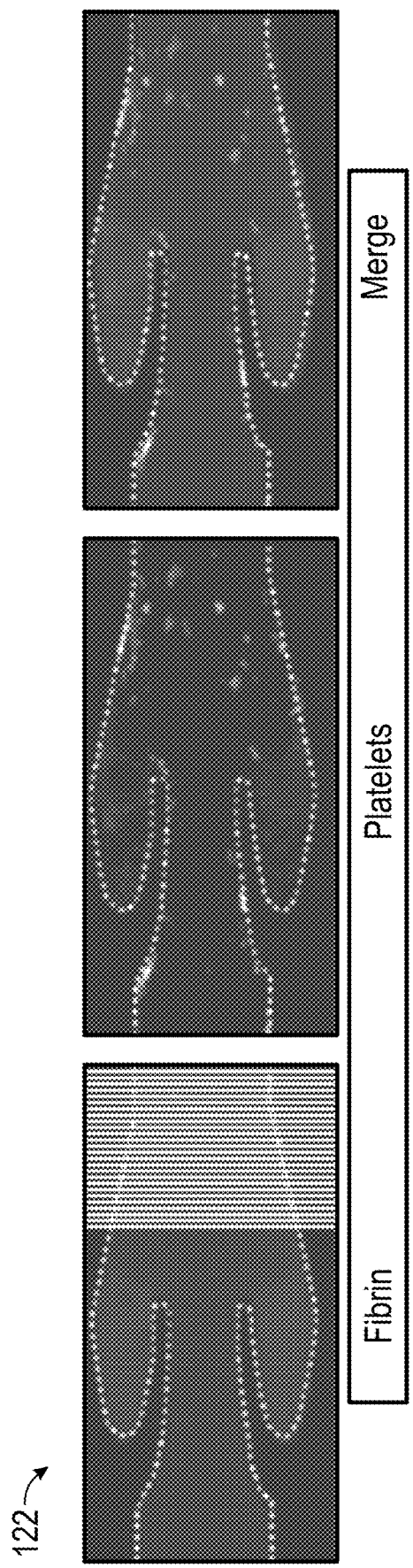
Figure 38:
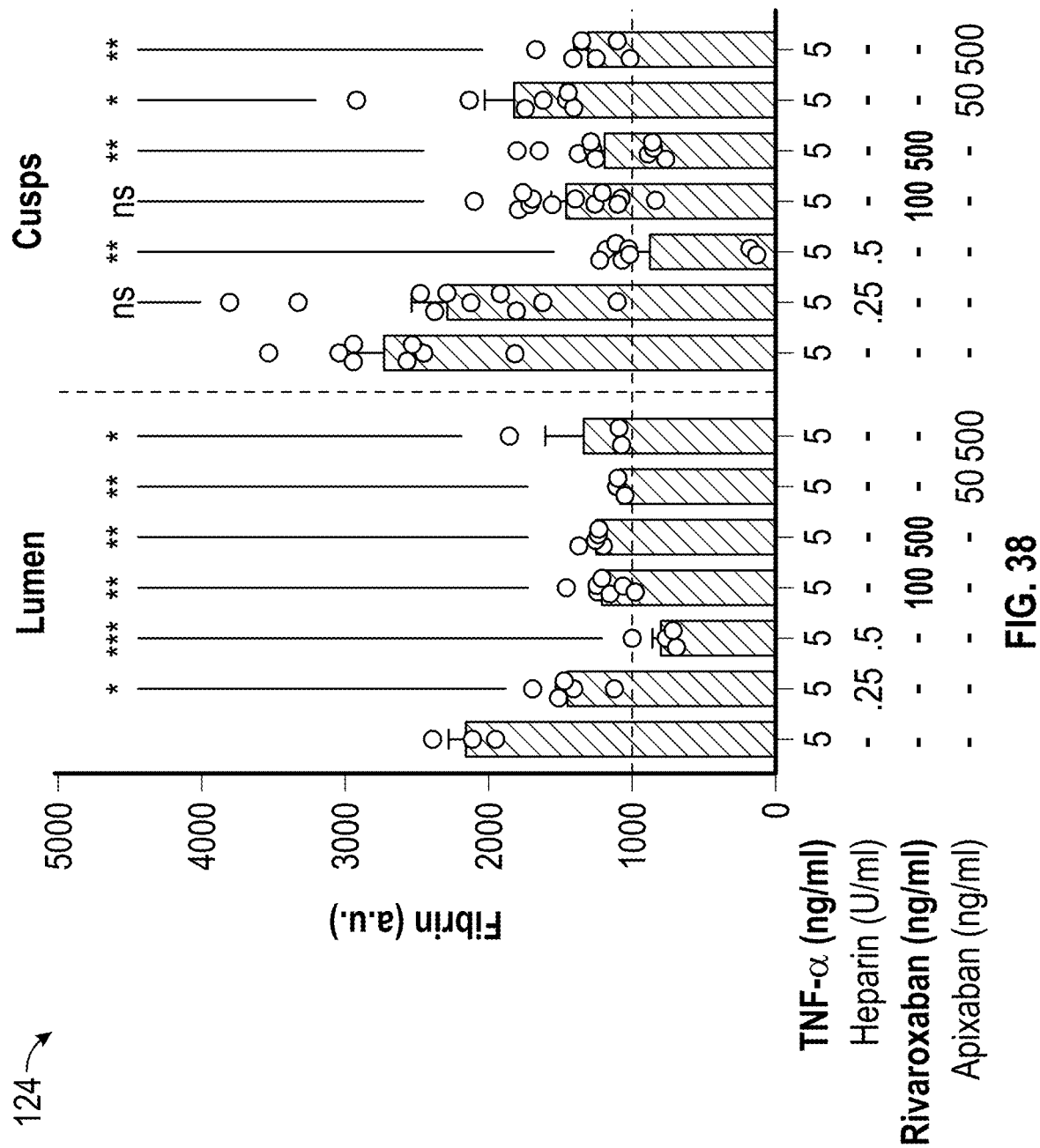
FIG. 38 is a graph illustrating experimental data pertaining to the venous valve shown in FIGS. 36, 37.
Figure 39:
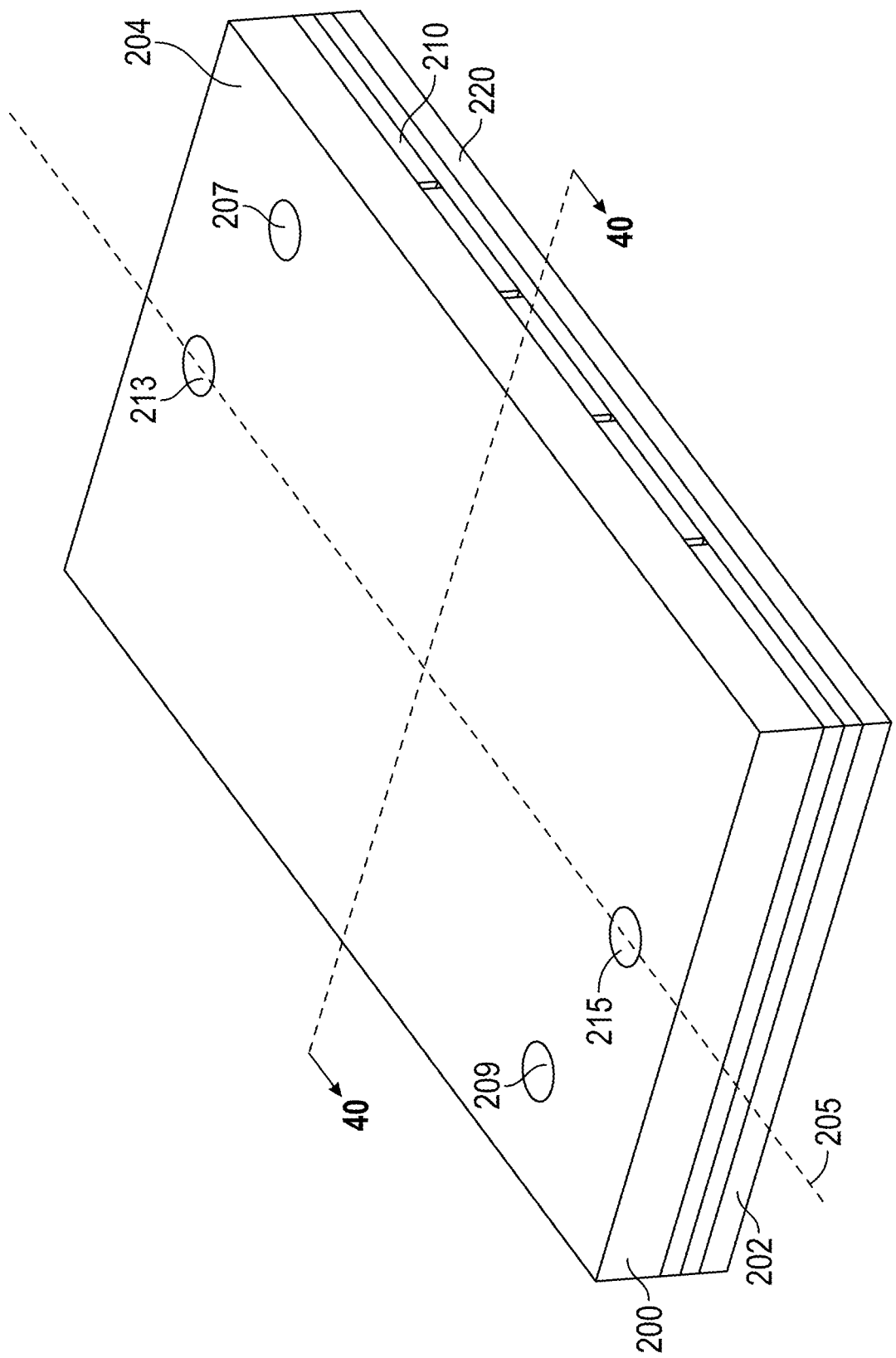
FIG. 39 is a perspective view of an embodiment of a macroscale actuating venous valve model in accordance with principles disclosed herein.
Figure 40:
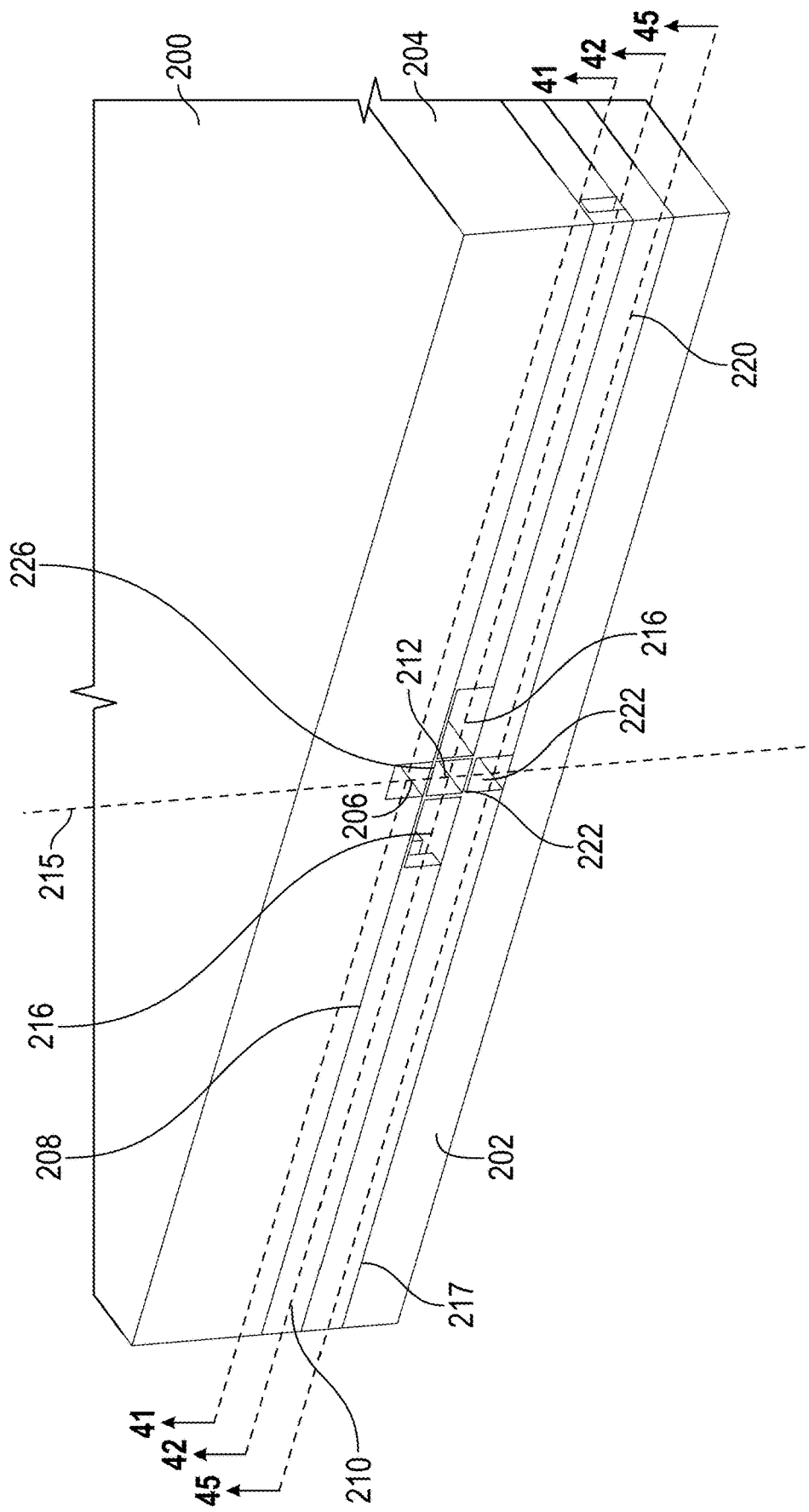
FIG. 40 is a cross-sectional view of the actuating venous valve model of FIG. 39 along line 40-40 of FIG. 39.
Figure 41:
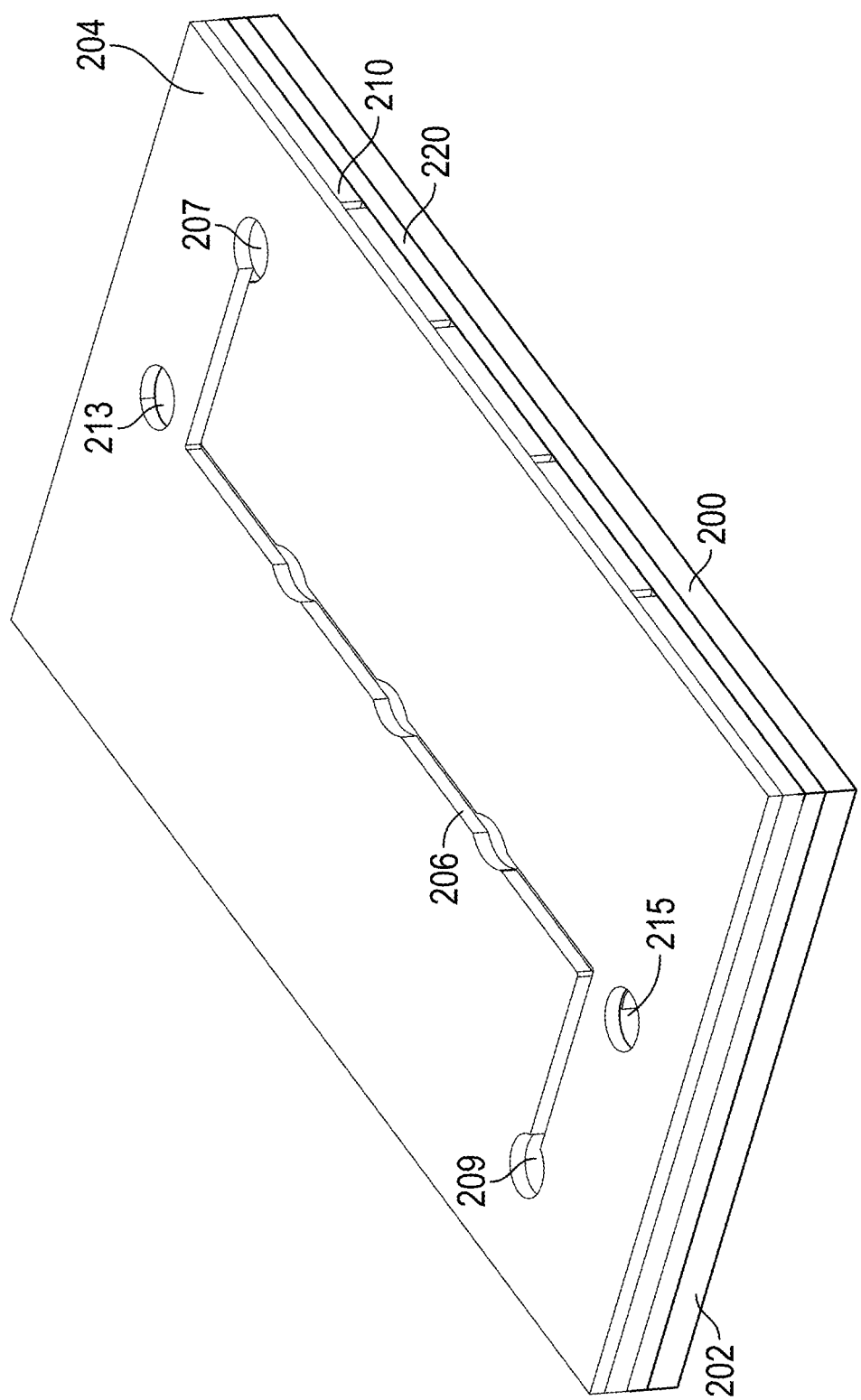
FIG. 41 is a cross-sectional view of the venous valve model of FIG. 39 along line 41-41 of FIG. 40.
Figure 42:
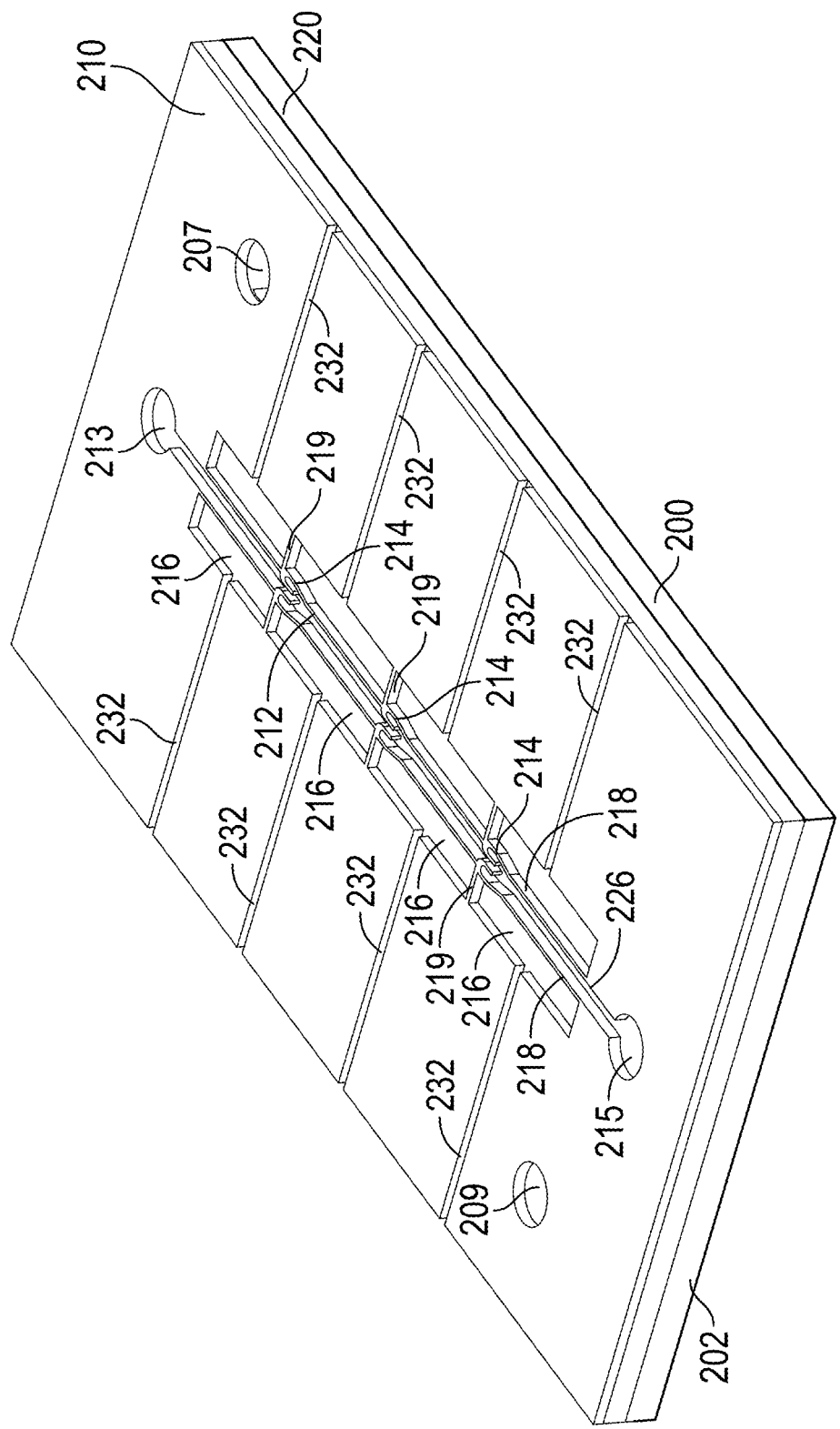
FIG. 42 is a cross-sectional view of the venous valve model of FIG. 39 along line 42-42 of FIG. 40.
Figure 43:
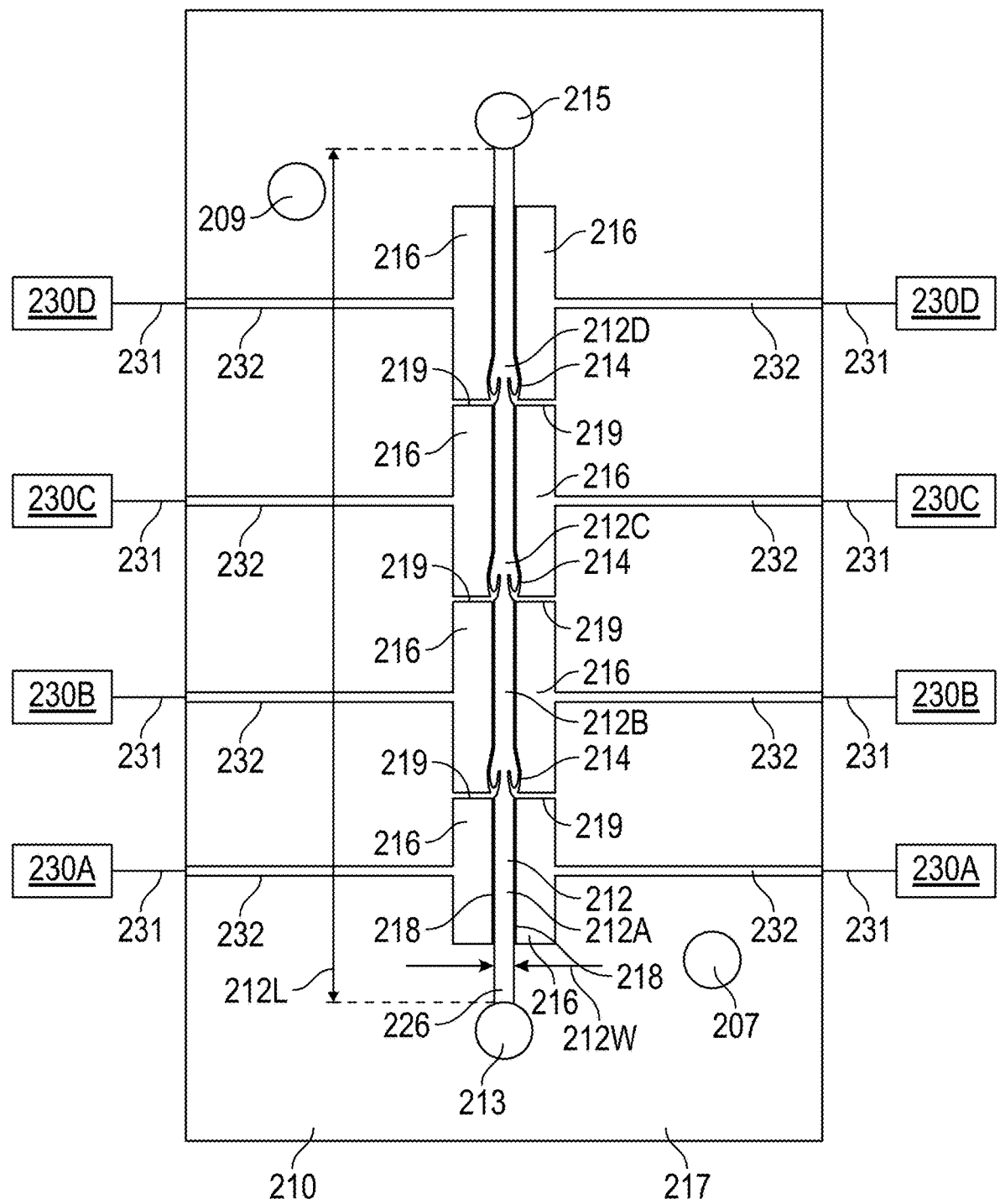
FIG. 43 is a bottom view of an embodiment of a central layer of the venous valve model of FIG. 39 in accordance with principles disclosed herein.
Figure 44:
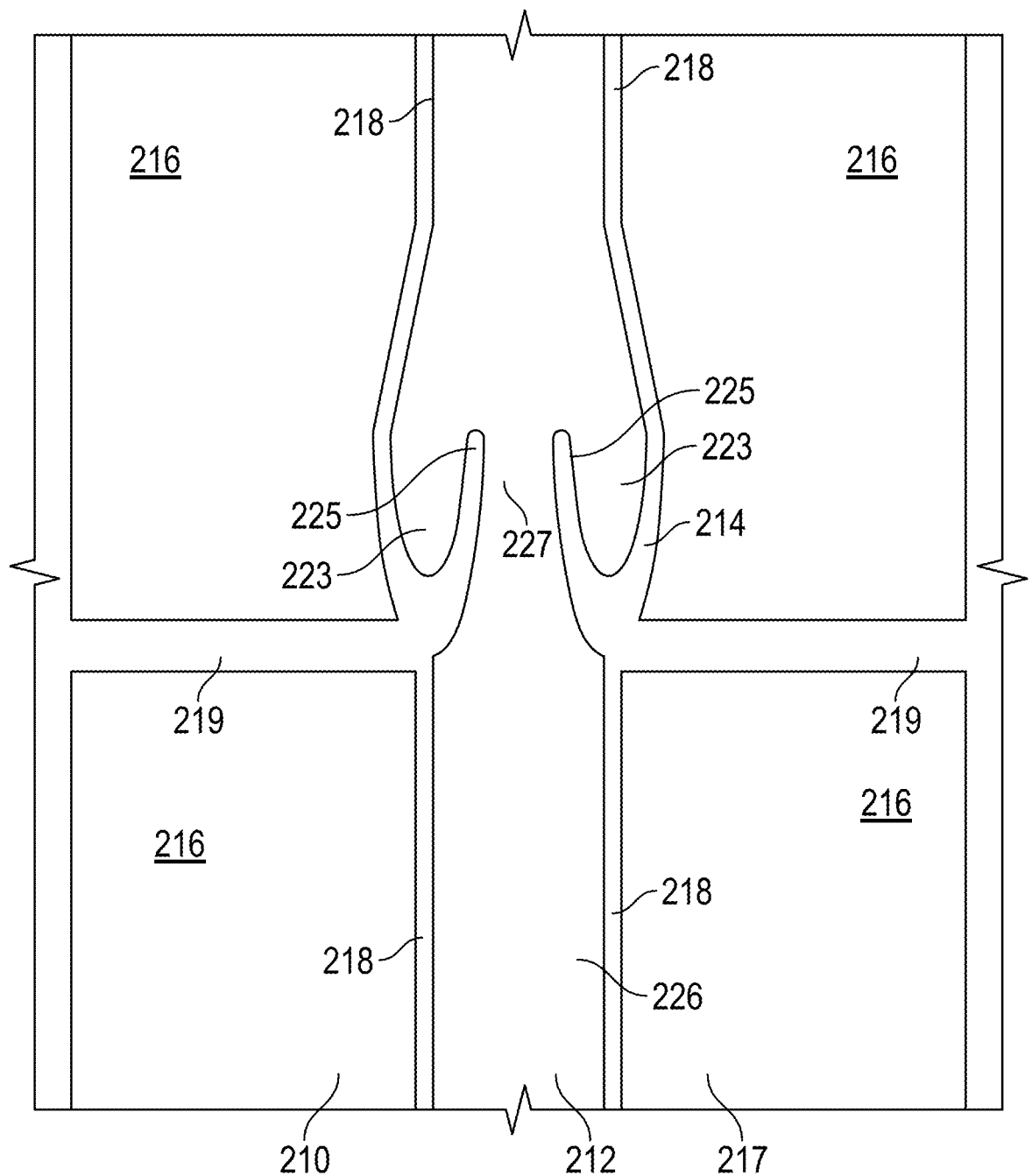
FIG. 44 is a bottom view of an embodiment of a venous valve of the central layer of FIG. 43 in accordance with principles disclosed herein.
Figure 45:
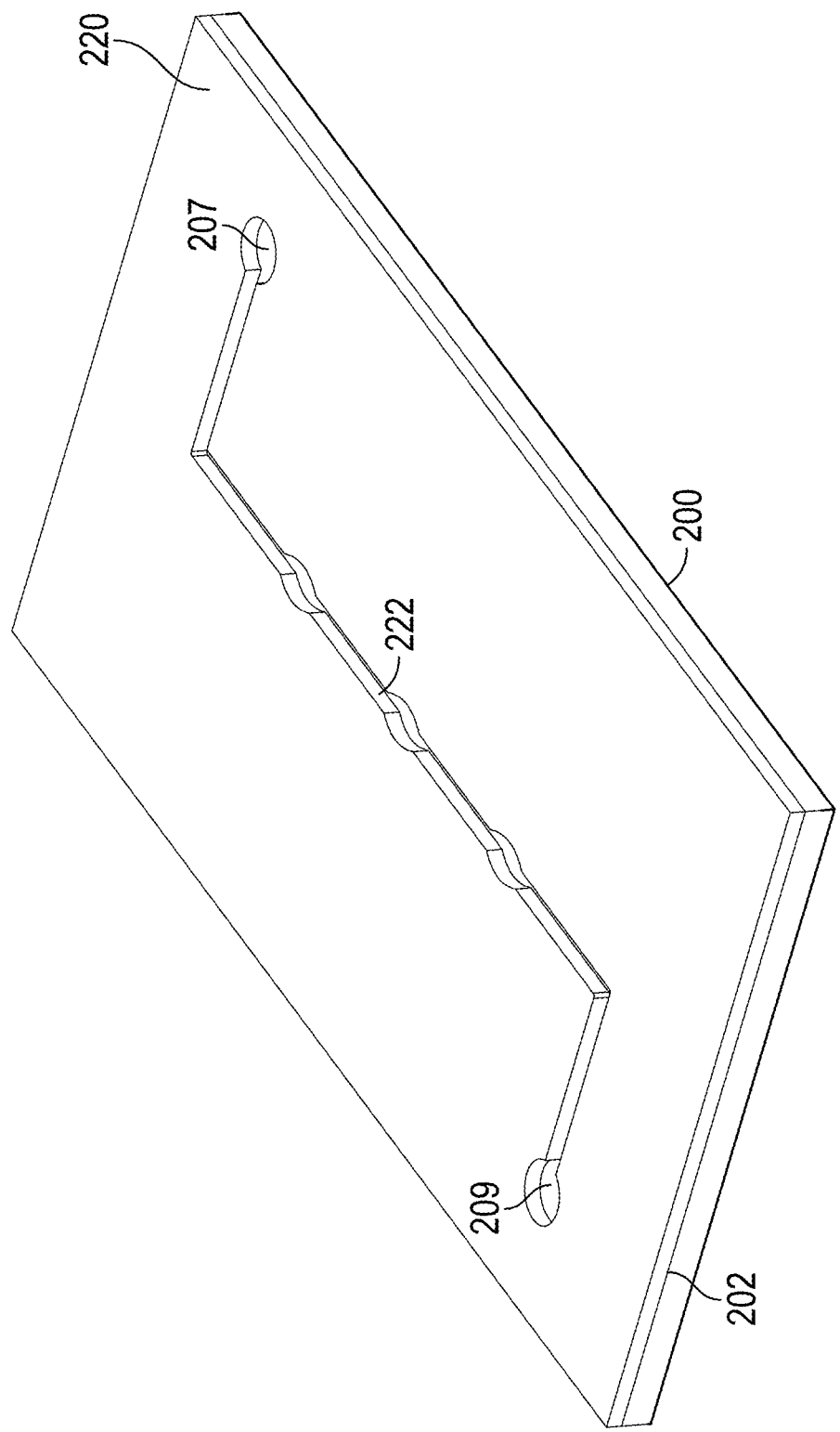
FIG. 45 is a cross-sectional view of the venous valve model of FIG. 39 along line 45-45 of FIG. 40.

Conventional treatment of DVT often includes the prescription of anticoagulants, which alters blood chemistry. However, there is no general clinical consensus upon the type and dosage of anticoagulant that is best suited to treat DVT and often treatment with anticoagulants significantly increases the risk of bleeding in patients. Embodiments of the microfluidic chip 40 may be utilized to assess anticoagulation therapy in DVT. Referring to FIGS. 36-38, images 120, 122 are shown of embodiments of venous valve 50B (treated with TNF-α at a dosage of 5 ng/ml) perfused with blood treated with Heparin lock flush, an intravenously administered drug that inactivates coagulation factors. Particularly, image 120 illustrates venous valve 50B perfused with blood treated with Heparin having a dosage of approximately 0.25 International Units per milliliter (IU/ml) while image 122 illustrates venous valve 50B perfused with blood treated with Heparin having a dosage of 0.50 IU/ml. Additionally, a graph 124 shown in FIG. 38 illustrates experimental data derived from the perfusion of Heparin treated blood through venous valve 50B as shown in FIGS. 36, 37.

In the example of FIGS. 33-38, thrombi formed in microfluidic channels 44A-44C reduced significantly when the dosage of Heparin was increased, as shown in graph 124 of FIG. 38. However, while a reduction in fibrin resulted even at a lower dose of Heparin within microfluidic model 40, fibrin in cusps 52 only reduced at the higher Heparin dosage (0.50 IU/ml in this example). The data provided by graph 124 indicates that venous cusps (e.g., cusps 52) may require higher Heparin anticoagulation than the systemic heparin anticoagulation to completely prevent the formation of local thrombi.

As shown particularly in the graph 124 of FIG. 38, embodiments of venous valve 50B were also perfused with blood treated by Rivaroxaban (at dosages of 100 ng/ml and 500 ng/ml), and blood treated with Apixaban (at dosages of 50 ng/ml and 500 ng/ml), each of which comprise clinically-prescribed direct oral anticoagulants (DOACs) that are potent antithrombotic drugs configured to inhibit factor Xa. In this example, when added to blood samples and introduced into an embodiment of venous valve 50B treated with TNF-α, fibrin rich clots were present in cusps 52 at the standard dosage for each DOAC (100 ng/ml of Rivaroxaban and 50 ng/ml of Apixaban, respectively) while there were unobservable thrombi in the luminal portion of the microfluidic model 40. Further, only when the dosage of each DOAC was increased to 500 ng/ml, were thrombi detected at cusps 52 and at the microfluidic channel 44B. Taken together, microfluidic model 40 validated the role of blood plasma chemistry as a Virchow factor that regulates DVT and predicted that standard-of-care anticoagulant therapy may resolve vein thrombosis mostly when prescribed at high doses, thus making patients more vulnerable to bleeding.

The present disclosure is also directed towards a three-dimensionally (3D)-printed fabrication technique for creating a 3D-printed vein or macroscale model of venous architecture having the same or similar dimensions as an in vivo human vein (e.g., the length of a side of the printed vein equals, or is similar to, the diameter of an in vivo vein). Additionally, in some embodiments, the 3D printed vein is integrated with mechanical and electrical instrumentation that can actuate, modulate, and predict the contractile (pumping) phenomena of the veins as well as pulsatile blood flow through the macroscale model. Further, the 3D-printed vein may be applied for studying the blood rheology, flow, initiation of clots and anticoagulant dosage in DVT.

In some embodiments, a macroscale model of a human vein may be formed using a CAD model (created via, e.g., the SolidWorks™ software package) having a square cross-section and comprising a scaled-up version of microfluidic chip 40 matching the dimensions of a human vein. As will be described further herein, the macroscale model may be provided with compartments on either side of a central channel and fabricated by 3D printing. The compartments may incorporate dynamic actuation to mimic the actuation and pumping of blood observed in human veins. Embodiments of the macroscale model may comprise an approximately 12 cm long central channel having an approximately 6 mm by 6 mm square cross-section. Embodiments of the macroscale model may be 3D printed on, for example, a Stratasys® Connex™ 500 multi-material printer using TangoPlus™ printing material, or other similar instrumentation and materials.

Additionally, in an exemplary embodiment for forming a macroscale model of a human vein, CFD simulations and nonlinear static structural simulations were conducted using CFD and finite element analysis (FEA) software, such as ANSYS@ Fluent and ANSYS@ Mechanical APDL, respectively, to determine the contour shape of the central channel of the macroscale model which when actuated compresses and simultaneously opens venous valves of the macroscale model. A CAD model of the macroscale model may be built using a CAD software package (e.g., the SolidWorks™ software package) and converted into a 3D-printable stereolithography (STL) format. Embodiments of the macroscale model may be fabricated with VeroWhite™ and TangoPlus™ printing materials. Particularly, embodiments of the macroscale model comprise a central channel having side walls printed with VeroWhite™, and top and bottom faces printed with TangoPlus™.

Referring to FIGS. 39-45, an embodiment of a 3D printed macroscale, in vivo human venous valve model 200 is shown. Venous valve model 200 has a central or longitudinal axis 205 and generally includes a body 202 including an upper layer 204 (shown particularly in FIG. 41), a central layer 210 (shown particularly in FIGS. 42-44), and a lower layer 220 (shown particularly in FIG. 45). Upper layer 204 of venous valve model includes an upper air channel 206 having a generally square cross-section, central layer 210 includes a central fluid channel 212 having a generally square cross-section and which extends adjacent the upper air channel 206 of upper layer 204, and lower layer 220 includes a lower air channel 222 having a generally square cross-section which extends adjacent the fluid channel 212 of central layer 210.

In this embodiment, upper air channel 206 and lower air channel 222 are each in fluid communication with an air inlet 207 and an air outlet 222 of venous valve model 200, where air inlet 207 and air outlet 209 each extend orthogonal central axis 205. In some embodiments, air inlet 207 may be in communication with a pressure regulator (not shown in FIGS. 39-45), to provide a predetermined air pressure within channels 207, 209. In some embodiments, an air pressure of approximately between eight and 11 kilopascals (kPa) may be provided in air channels 206, 222. Air channels 206, 222 extend parallel with fluid channel 212 and, as shown particularly in FIG. 40, air channels 206, 222 each lie within the same vertical plane 215 (plane 215 extending orthogonal central axis 205) as fluid channel 212. Also as shown particularly in FIG. 40, upper air channel 206 extends entirely through a bottom face 208 of upper layer 204, and thus air within upper air channel 206 contacts and acts directly against an upper wall 226 of fluid channel 212. Additionally, in this embodiment, fluid channel 212 extends through a bottom face 217 of central layer 210, and thus fluid within fluid channel 212 contacts and acts directly against an upper wall 228 of lower air channel 222. In some embodiments, walls 226, 228 may each be approximately 20 μm thick.

In the embodiment of FIGS. s39-45, fluid channel 212 of central layer 220 extends parallel with central axis 205 and extends from a fluid inlet 213 and a fluid outlet 215 opposite fluid outlet 213. In some embodiments, fluid channel 212 may be aligned with central axis 205 whereby a plane extends through both fluid channel 212 and central axis 205. Fluid channel 212 includes three actuatable venous valves 214, each of which may be selectably opened and closed to control the flow of fluid through fluid channel 212. Additionally, central layer 210 includes a plurality of actuation channels or compartments 216.

In vivo deep human veins are generally actuated by the surrounding muscles in which the vein lies. In this embodiment, the actuation of venous valve model 200 is achieved by the actuation of actuation compartments 216 that are separated from fluid channel 212 by walls 218 that are approximately 250 μm in thickness. Actuation compartments 216 on either side of fluid channel 212 are further divided into four parts by thin separating walls 219 approximately 250 μm in thickness. Separating walls 219 are placed near venous valves 214 such that each actuation compartment 216 is partially defined by one of the walls 218 of fluid channel 212 and a pair of separating walls 219, where wall 218 of fluid channel 212 extends between the pair of separating walls 219 and adjacently positioned venous valves 214. In this embodiment, fluid channel 212 has a length 212L extending from fluid inlet 213 to fluid outlet 213 that is approximately 2 cm, and a width 212W extending between walls 218 that is approximately 200 μm In this embodiment, each actuation compartment 216 is in fluid communication with one of a plurality of pumps 230A-230D (shown schematically in FIG. 43) via a channel 232 extending orthogonal central fluid channel 212. In some embodiments, each pump 230A-230D may comprise a syringe pump such as a Harvard apparatus; however, in other embodiments, pumps 230A-230D may comprise other types of pumps, including commercially available vacuum pumps. In this embodiment, each pump 230A-230D is connected to a corresponding channel 232 via tubing 231 having an inner diameter of approximately 0.5 millimeter (mm). In this configuration, when one of the pumps 230A-230D is actuated in a withdraw mode, the actuated pump 230A-230D will dilate the portion of the fluid channel 212 located adjacent the actuation compartment 216 in fluid communication with the actuated pump 230A-230D by deforming the wall 218 separating the actuation compartment 216 and the fluid channel 212. Similarly, when one of the pumps 230A-230D is actuated in an infusion mode, the actuated pump 230A-230D will compress the portion of fluid channel 212 located adjacent the actuation compartment 216 in fluid communication with the actuated pump 230A-230D.

In this embodiment, venous valve model 200 comprises three venous valves 214 and four linear sections 212A-212D (shown in FIG. 43) of fluid channel 212; however, in other embodiments, the number of venous valves 214 and sections 212A-212D of fluid channel 212 may vary. When each wall 218 of the same section 212A-212D (e.g., section 212B in this example) of fluid channel 212 are compressed, some of the fluid (blood or blood mimicking fluids) inside section 212B of fluid channel 212 is displaced or pumped forward into section 212C (located immediately downstream from section 212B) via the actuation of pumps 230B into the infusion mode while the remainder of the fluid in section 212B of fluid channel 212 is displaced or forced upstream in the direction of section 212A (positioned immediately upstream from section 212B of fluid channel 212). The portion of the fluid displaced downstream flows through the venous valve 214 positioned between sections 212B, 212C and into section 212C of fluid channel 212. The portion of the fluid displaced upstream from the compressed portion of fluid channel 212 flows into the cusps 223 (shown in FIG. 44) of the venous valves 214 positioned between sections 212A, 212B to trap and thereby restrict the fluid from flowing into section 212A of fluid channel 212. Particularly, each venous valve comprises a pair of valve leaflets 225 defining cusps 223, and a central flow channel 227 extending between the pair of leaflets 225. Thus, cusps 223 of venous valves 213 enable the unidirectional flow of fluid through venous valve model 200 as seen in vivo. Air channels 206 and 222 of venous valve model 200 permit deformation of fluid channel 212 to thereby assist with the flowing of fluid through fluid channel 212 via venous valves 214.

In some embodiments, venous valves 214 are actuated (opened and closed) by contracting and dilating sections 212A-212D of fluid channel 212 in an alternating manner.

For example, pumps 230A, 230C may be actuated in the infusion mode to contract sections 212A, 212C of fluid channel 212 while pumps 230B, 230D are actuated in the withdraw mode to dilate sections 212B, 212D of fluid channel 212. The alternating contraction and dilations assists with one way pumping of the fluid in fluid channel 212. In this embodiment, a 3D printable fixture or pumping system 250 (shown schematically in FIG. 43) may be used to modify the working of one or more of pumps 230A-230D to achieve the alternating actuation of fluid channel 212. For example, the pumping system 250 may accommodate two syringes within it, with the pumping system 250 acting to drive one syringe opposite to the other, i.e. when one syringe is in withdraw mode the other will be in infusion mode and vice versa. One of the syringes may be connected to the actuation compartments 216 corresponding to sections 212A, 212C of fluid channel 212 while the other syringe may be attached to the actuation compartments 216 corresponding to sections 212B, 212D of fluid channel 212. In other words, pumps 230A, 230C may comprise a first syringe of the pumping system 250 while pumps 230B, 230D may comprise a second syringe of the pumping system 250.

In this embodiment, endothelial cells were grown on the walls (including upper wall 226) of the fluid channel 212 of an embodiment of venous valve model 200 to form confluent lumen that mimics in-vivo blood vessel physiology. Also, media was perfused in these channels for an approximately twenty-four hour period at constant and pulsatile venous flow rates to induce wall shear stress similar to that experienced by endothelial cells in the in vivo deep veins. The cells were then treated with different doses of cytokines (e.g., 0 ng/ml, 5 ng/ml and 100 ng/ml for about eighteen hours) to recapitulate the physiology of diseased and healthy venous valves before perfusing blood derived from healthy individuals and diseased patients.

Conventional techniques for modeling human veins generally comprise the use of animal models which do not mimic the anatomy, physiology and biophysics of venous architecture and flow. Therefore, attempting drug discovery with these models is not predictive. The microfluidic and macroscale models (e.g., microfluidic model 40 and venous valve model 200) described herein may address some of the limitations of conventional modeling techniques. For example, the microfluidic and macroscale models described herein may be made in vitro with materials and techniques that permit convenient analysis of the biology of venous flow and vessel using microscopy and other biochemical assays. Additionally, the in vitro microphysiological model (e.g., microfluidic chip 40) of deep veins may recapitulate the in vivo microphysiology faithfully. As described above, the fluid flow pattern, recirculations and secondary vortices were recreated in embodiments of microfluidic model 40 similar to that observed in vivo. As low as 20 ul of blood was enough to carry out a single experiment with embodiments of microchannels 44A-44C as channels each only have a volume of approximately 0.3 ul. Further, a bioprinted macroscale model of a human vein (e.g., venous valve model 200) was created with functioning, actuatable valves. The compression of the channel walls (e.g., walls 218 of fluid channel 212) led to the opening of the venous valves (e.g., valves 214) and expansion of the channel walls led to the closing of the venous valves thus mimicking the actuation mechanism found in vivo. The macroscale model was also able to include mechanical stimulus on top of flow induced shear stress to the cells if cells are cultured in these channels.

DVT and subsequent pulmonary embolism (PE) causes about 200,000 deaths in the US annually. The models and processes described herein may be used to develop a clinical device which will give a patient specific readout for propensity for thrombogenesis. The models described herein may also be used in preclinical trials of new anticoagulant drugs in place of animal models and human volunteers. The pharmaceutical industry may use the models described herein for identifying mechanisms of action of drugs, compounds and molecules that may have therapeutic or toxic effects on human body.

Conventional models used in preclinical trials of new anticoagulant drugs often comprise human volunteers and in vivo animal models. For example, the most common animal model of thrombosis is the murine model in which venous thrombosis is induced slowly by stasis or stenosis (both by ligation) or rapidly by an acute injury (using free-radicals) of the inferior vena cava. Though these diverse mouse models have contributed immensely in decoding several key mechanisms that govern thrombosis, capturing the thrombus dynamics in human-relevant conditions, as well as effective in studying the role of genetic variation and different clotting factors in thrombus formation, the physiological and genetic differences of these models with respect to humans limits them considerably, as evidenced by the fact several drug trials that succeeded in such animal models have failed in human clinical trials, thus contributing to high healthcare costs.

In addition, there is inherent risk of bleeding to human volunteers during their participation in the preclinical trials for testing new anticoagulant drugs. Further, a widely used tool to assess and determine if a patient has to receive thromboprohylaxis is to use risk scores, such as Khorana, PROTECHT, Vienna CATS, CONKO etc. The Khorana score, for example, gives a score based on the patient's cancer type, BMI, leukocyte count, platelet count and hemoglobin level, and if the score is above three, the patient has a high propensity to get DVT. One of the main limitations with these scores is their predictive performance may be limited and does not include the factors that enhances thrombus formation like coagulation factors.

The models and processes disclosed herein (e.g., microfluidic model 40 and venous valve model 200) create human physiology outside of human body to test new anticoagulant drugs. Thus, use of animals and human volunteers in the preclinical and clinical trials may be reduced. The models disclosed herein may also be used for thromboprophylaxis and anticoagulant drug dosage from a readout by perfusing patient derived blood. While conventional parallel plate flow chambers have been useful in studying the effects of shear and recirculating flow on platelet function and coagulation, accurate blood vessel anatomy and flow patterns are not replicated in these conventional devices. Models disclosed herein however include accurate blood vessel anatomy and the complex flow pattern observed in vivo that are relevant to DVT formation. Conversely, conventional cone-and-plate viscometers are often bulky and need large amounts of blood, cultured cells and reagents for each experiment, making them low throughput. Also, the experiments in these conventional devices are typically conducted over two-dimensional (2D) monolayers of proteins or cells and therefore, they do not mimic the function of a 3D round vascular lumen and natural blood flow. At least some of these limitations are addressed in the models disclosed herein. For example, embodiments of microfluidic model 40 only requires a few microliters of blood and reagents are needed for each experiment and only about 10 million cells are needed to form a 3D confluent lumen of endothelial cells in an approximately twenty-four hour period. The macroscale model (e.g., venous valve model 200) also accurately simulates the mechanical strains that are experienced by the endothelial cells in vivo.

Extensive simulations of the fluid flow in the microfluidic channels (e.g., microchannels 44A-44C) have been carried out and the results support the formation of disturbed flow and vortices in the venous valve design. Endothelial cells were cultured in these channels and blood was perfused at venous shear rates which resulted in free flow of blood without any clot formation. This suggests that an intact lumen was formed in the channel as observed in vivo. When the lumen was treated with varying doses of cytokines (TNF-α), fibrin rich clots were predominantly formed in the venous valve cusps as observed in vivo. Additionally, the simulations of flow and actuation of the macroscopic model (e.g., venous valve model 200) using computational fluid dynamics and structural assessment software tools have given positive results.

While exemplary embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A microfluidic chip for modelling flow through a vein, comprising:
    an artificially fabricated body comprising a microchannel extending between a fluid inlet and a fluid outlet, wherein at least a portion of the microchannel is coated with endothelial cells that form vascular lumen; and
    a venous valve formed in the artificially fabricated body and positioned along the microchannel, wherein the venous valve comprises a pair of leaflets defining a pair of cusps of the venous valve, and a flow channel positioned between the leaflets.

2. The microfluidic chip of claim 1, wherein the endothelial cells comprise human umbilical vein endothelial cells (HUVECs).

3. The microfluidic chip of claim 2, wherein the HUVECs are coated over a layer of an extracellular matrix (ECM).

4. The microfluidic chip of claim 1, wherein the vascular lumen is treated with tumor necrosis-factor alpha (TNF-α) at a dosage of less than 300 nanograms per milliliter (ng/ml).

5. The microfluidic chip of claim 1, wherein at least a portion of the pair of cusps is coated with the endothelial cells that form the vascular lumen.

6. The microfluidic chip of claim 1, wherein a width of the flow channel of the venous valve is between 25 micrometers (μm) and 200 μm.

7. The microfluidic chip of claim 1, wherein the artificially fabricated body is formed from Polydimethylsiloxane (PDMS).

8. A method of forming a microfluidic chip for modelling flow through a vein, comprising:
    (a) forming a microchannel and a venous valve positioned along the microchannel in a master mold, wherein the venous valve comprises a pair of leaflets defining a pair of cusps of the venous valve, and a flow channel positioned between the leaflets; and
    (b) coating at least a portion of the microchannel with endothelial cells that form vascular lumen.

9. The method of claim 8, wherein the endothelial cells comprise human umbilical vein endothelial cells (HUVECs) coated over a layer of an extracellular matrix (ECM).

10. The method of claim 8, wherein (b) comprises treating the vascular lumen with tumor necrosis-factor alpha (TNF-α) at a dosage of less than 300 nanograms per milliliter (ng/ml).

11. A microfluidic chip for modelling flow through a vein, comprising:
    an artificially fabricated body having a central axis and a fluid channel extending between a fluid inlet and a fluid outlet formed in the artificially fabricated body, wherein the fluid channel is defined by a pair of channel walls, and wherein at least a portion of the fluid channel is coated with endothelial cells that form vascular lumen;
    wherein a first venous valve is formed in the artificially fabricated body and positioned along the fluid channel, the first venous valve comprising a pair of leaflets defining a pair of cusps of the first venous valve and a flow channel positioned between the leaflets; and
    wherein a pair of first actuation chambers is positioned adjacent the channel walls of the fluid channel, wherein the pair of first actuation chambers are configured to decrease a width of the flow channel of the first venous valve in response to pressurization of the pair of first actuation chambers, and to increase a width of the flow channel of the first venous valve in response to depressurization of the pair of first actuation chambers.

12. The microfluidic chip of claim 11, wherein the artificially fabricated body is formed from a three-dimensionally printed material.

13. The microfluidic chip of claim 11, wherein the first venous valve comprises a flow channel positioned between the leaflets.

14. The microfluidic chip of claim 11, wherein:
    the pair of first actuation chambers are positioned adjacent a first section of the fluid channel;
    the artificially fabricated body further comprises a pair of second actuation chambers positioned adjacent a second section of the fluid channel located between the first section and the fluid outlet, and wherein the first venous valve is positioned between the first section and the second section; and
    the leaflets of the first venous valve are configured to direct fluid within the second section of the fluid channel into the cusps of the first venous valve in response to pressurization of the pair of second actuation chambers.

15. The microfluidic chip of claim 14, wherein the artificially fabricated body comprises a pair of chamber walls positioned between the first pair of actuation chambers and the second pair of actuation chambers, wherein the pair of chamber walls restrict fluid communication between the first pair of actuation chambers and the second pair of actuation chambers.

16. The microfluidic chip of claim 11, wherein the artificially fabricated body comprises:
   a first air channel extending parallel with the fluid channel; and
   a second air channel extending parallel with the fluid channel, wherein the first air channel, the second air channel, and the fluid channel are each intersected by a plane extending orthogonally from the central axis.

17. A venous valve model, comprising:
   the microfluidic chip of claim 11; and
   a pump in fluid communication with at least one of the pair of first actuation chambers, wherein the pump comprises an infusion mode configured to increase a pressure within the at least one of the pair of first actuation chambers to decrease the width of the fluid channel, and a withdraw mode configured to decrease a pressure within the at least one of the pair of first actuation chambers to increase the width of the fluid channel.

18. The venous valve model of claim 17, wherein the pump comprises a syringe pump.

19. The venous valve model of claim 18, wherein:
   the pair of first actuation chambers of the microfluidic chip are positioned adjacent a first section of the fluid channel;
   the artificially fabricated body of the microfluidic chip further comprises a pair of second actuation chambers positioned adjacent a second section of the fluid channel located between the first section and the fluid outlet, and wherein the first venous valve is positioned between the first section and the second section;
   the leaflets of the first venous valve of the microfluidic chip are configured to direct fluid within the second section of the fluid channel into the cusps of the first venous valve in response to pressurization of the pair of second actuation chambers;
   the syringe pump comprises a first syringe pump and the venous valve model further comprises a second syringe pump in fluid communication with at least one of the pair of second actuation chambers of the microfluidic chip;
   the second syringe pump comprises an infusion mode configured to increase a pressure within the at least one of the pair of second actuation chambers to decrease the width of the fluid channel, and a withdraw mode configured to decrease a pressure within the at least one of the pair of second actuation chambers to increase the width of the fluid channel; and
   the second syringe pump is configured to occupy the withdraw mode when the first syringe pump is in the infusion mode and to occupy the infusion mode when the first syringe pump is in the withdraw mode.

20. A venous valve model, comprising:
   the microfluidic chip of claim 14, wherein a pair of third actuation chambers is positioned adjacent a third section of the fluid channel located between the second section and the fluid outlet, and a second venous valve is formed in the artificially fabricated body and positioned between the second section and the third section; and
   a pumping system comprising a plurality of pumps and configured to simultaneously pressurize the first section and the third section of the fluid channel and depressurize the second section of the fluid channel.

* * * * *